(12) United States Patent
Incisivo et al.

(10) Patent No.: US 11,396,533 B2
(45) Date of Patent: Jul. 26, 2022

(54) PROCESS FOR THE MANUFACTURE OF GLP-1 ANALOGUES

(71) Applicant: FRESENIUS KABI IPSUM S.R.L., Cassina de' Pecchi—Milano (IT)

(72) Inventors: Giuseppina Maria Incisivo, Villadose (IT); Andrea Orlandin, Villadose (IT); Antonio Ricci, Villadose (IT); Ivan Guryanov, Villadose (IT); Walter Cabri, Villadose (IT)

(73) Assignee: FRESENIUS KABI IPSUM S.R.L., Milan (IT)

(*) Notice: Subject to any disclaimer, the term of this patent is extended or adjusted under 35 U.S.C. 154(b) by 0 days.

(21) Appl. No.: 17/283,937

(22) PCT Filed: Oct. 9, 2019

(86) PCT No.: PCT/EP2019/077367
§ 371 (c)(1),
(2) Date: Apr. 8, 2021

(87) PCT Pub. No.: WO2020/074583
PCT Pub. Date: Apr. 16, 2020

(65) Prior Publication Data
US 2022/0041680 A1 Feb. 10, 2022

(30) Foreign Application Priority Data
Oct. 9, 2018 (EP) .................................... 18199401

(51) Int. Cl.
C07K 14/605 (2006.01)
C07K 1/04 (2006.01)
C07K 1/06 (2006.01)

(52) U.S. Cl.
CPC ............ *C07K 14/605* (2013.01); *C07K 1/042* (2013.01); *C07K 1/062* (2013.01)

(58) Field of Classification Search
CPC ....... C07K 14/605; C07K 1/042; C07K 1/062
See application file for complete search history.

(56) References Cited

U.S. PATENT DOCUMENTS

| | | |
|---|---|---|
| 3,642,763 A | 2/1972 | Wunsch et al. |
| 4,826,763 A | 5/1989 | Norris et al. |
| 6,110,703 A | 8/2000 | Egel-Mitani et al. |
| 2008/0004429 A1* | 1/2008 | Roberts ................ C07K 14/605 530/330 |

FOREIGN PATENT DOCUMENTS

| | | |
|---|---|---|
| CN | 103 333 239 A | 10/2013 |
| CN | 104004083 A | 8/2014 |
| CN | 104356224 A | 2/2015 |
| CN | 104650219 B | 11/2017 |
| WO | WO 2007/147816 A1 | 12/2007 |
| WO | WO 2010/070255 A1 | 6/2010 |
| WO | WO 2015/028966 A2 | 3/2015 |
| WO | WO 2016/046753 A1 | 3/2016 |
| WO | WO 2017/127007 A1 | 7/2017 |
| WO | WO 2017/162650 A1 | 9/2017 |

OTHER PUBLICATIONS

Anonymous, "Process for the Preparation of Semaglutide," IP.com, IPCOM000250955D, 5 pgs. (2017). http://ip.com/IPCOM/000250955D.
Cremer et al., "Combining a polar resin and a pseudo-proline to optimize the solid-phase synthesis of a 'difficult sequence'," *Journal of Peptide Science* 12(6): 437-442 (2006).
Guryanov et al., "Innovative chemical synthesis and conformational hints on the lipopeptide liraglutide," *Journal of Peptide Science* 16(10)SI: 575-581 and *Journal of Peptide Science* 22(7): 471-479 (2016).
Haack et al., "Serine Derived Oxazolidines as Secondary Structure Disrupting, Solubilizing Building Blocks in Peptide Synthesis," *Tetrahedron Letters* 33(12): 1589-1592 (1992).
Shelton et al., "Linkers, Resins, and General Procedures for Solid-Phase Peptide Synthesis," *Peptide Synthesis and Applications, Methods in Molecular Biology*, Knud J. Jensen et al. (eds.), vol. 1047, Chapter 2, pp. 23-41 (2013).
European Patent Office, International Search Report in International Application No. PCT/EP2019/077367 (dated Nov. 11, 2019).
European Patent Office, Written Opinion in International Application No. PCT/EP2019/077367 (dated Nov. 11, 2019).
U.S. Appl. No. 17/620,433, filed Dec. 17, 2021.
*Chemistry of Peptide Synthesis*, N. L. Benoiton, Editor, Tailor and Francis Group, 303 pages (2006).
International Bureau of WIPO, International Preliminary Report on Patentability in International Application No. PCT/EP2019/077367 (dated Apr. 8, 2021).

* cited by examiner

*Primary Examiner* — Sudhakar Katakam
(74) *Attorney, Agent, or Firm* — Leydig, Volt & Mayer, Ltd.

(57) ABSTRACT

The present invention provides a process for the manufacture of GLP-1 analogues with high yield and purity by fragment condensation on the solid phase. In particular, it describes a convergent synthesis by condensation of a C-terminal pseudoproline fragment A with a fragment B bound to a solid support, followed by deprotection and cleavage from the support and final purification to yield the desired peptide. The invention further provides intermediates useful in the manufacturing process.

15 Claims, No Drawings
Specification includes a Sequence Listing.

SEQUENCE LISTING

<160> NUMBER OF SEQ ID NOS: 20

<210> SEQ ID NO 1
<211> LENGTH: 31
<212> TYPE: PRT
<213> ORGANISM: Artificial Sequence
<220> FEATURE:
<223> OTHER INFORMATION: liraglutide
<220> FEATURE:
<221> NAME/KEY: MISC_FEATURE
<222> LOCATION: (20)..(20)
<223> OTHER INFORMATION: Lys(Pal-Glu)

<400> SEQUENCE: 1

His Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg Gly
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: semaglutide
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (20)..(20)
<223> OTHER INFORMATION: Lys(N-(17-carboxy-1-oxoheptadecyl)-L-glutamyl-
      2-[2-(2-aminoethoxy)ethoxy]acetyl-2-[2-(2-
      aminoethoxy)ethoxy]acetyl)

<400> SEQUENCE: 2

His Xaa Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg Gly
            20                  25                  30

<210> SEQ ID NO 3
<211> LENGTH: 8
<212> TYPE: PRT
<213> ORGANISM: Artificial Sequence
<220> FEATURE:
<223> OTHER INFORMATION: Synthetic fragment A (1-8)
<220> FEATURE:
<221> NAME/KEY: MISC_FEATURE
<222> LOCATION: (1)..(1)
<223> OTHER INFORMATION: Xaa is His, Boc-His, or Boc-His(Trt)
<220> FEATURE:
<221> NAME/KEY: MISC_FEATURE
<222> LOCATION: (2)..(2)
<223> OTHER INFORMATION: Xaa is Ala or Aib
<220> FEATURE:
<221> NAME/KEY: MISC_FEATURE
<222> LOCATION: (3)..(3)
<223> OTHER INFORMATION: Xaa is Glu or Glu(OtBu)
<220> FEATURE:
<221> NAME/KEY: MISC_FEATURE
<222> LOCATION: (5)..(5)
<223> OTHER INFORMATION: Xaa is Thr or Thr(tBu)
<220> FEATURE:
<221> NAME/KEY: MISC_FEATURE
<222> LOCATION: (7)..(7)
<223> OTHER INFORMATION: Xaa is Thr or Thr(tBu)
<220> FEATURE:
<221> NAME/KEY: MISC_FEATURE
<222> LOCATION: (8)..(8)
<223> OTHER INFORMATION: Xaa is Ser(psi-z,z-pro), Ser(psi-Me,Me-pro), or -continued

```
          Ser(psi-Me,Me-pro)-OH

<400> SEQUENCE: 3

Xaa Xaa Xaa Gly Xaa Phe Xaa Xaa
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic fragment A (1-11)
<220> FEATURE:
<221> NAME/KEY: MISC_FEATURE
<222> LOCATION: (1)..(1)
<223> OTHER INFORMATION: Xaa is His, Boc-His, or Boc-His(Trt)
<220> FEATURE:
<221> NAME/KEY: MISC_FEATURE
<222> LOCATION: (2)..(2)
<223> OTHER INFORMATION: Xaa is Ala or Aib
<220> FEATURE:
<221> NAME/KEY: MISC_FEATURE
<222> LOCATION: (3)..(3)
<223> OTHER INFORMATION: Xaa is Glu or Glu(OtBu)
<220> FEATURE:
<221> NAME/KEY: MISC_FEATURE
<222> LOCATION: (5)..(5)
<223> OTHER INFORMATION: Xaa is Thr or Thr(tBu)
<220> FEATURE:
<221> NAME/KEY: MISC_FEATURE
<222> LOCATION: (7)..(7)
<223> OTHER INFORMATION: Xaa is Thr or Thr(tBu)
<220> FEATURE:
<221> NAME/KEY: MISC_FEATURE
<222> LOCATION: (8)..(8)
<223> OTHER INFORMATION: Xaa is Ser or Ser(tBu)
<220> FEATURE:
<221> NAME/KEY: MISC_FEATURE
<222> LOCATION: (9)..(9)
<223> OTHER INFORMATION: Xaa is Asp or Asp(OtBu)
<220> FEATURE:
<221> NAME/KEY: MISC_FEATURE
<222> LOCATION: (11)..(11)
<223> OTHER INFORMATION: Xaa is Ser(psi-z,z-pro), Ser(psi-Me,Me-pro), or
      Ser(psi-Me,Me-pro)-OH

<400> SEQUENCE: 4

Xaa Xaa Xaa Gly Xaa Phe Xaa Xaa Xaa Val Xaa
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic fragment A (1-12)
<220> FEATURE:
<221> NAME/KEY: MISC_FEATURE
<222> LOCATION: (1)..(1)
<223> OTHER INFORMATION: Xaa is His, Boc-His, or Boc-His(Trt)
<220> FEATURE:
<221> NAME/KEY: MISC_FEATURE
<222> LOCATION: (2)..(2)
<223> OTHER INFORMATION: Xaa is Ala or Aib
<220> FEATURE:
<221> NAME/KEY: MISC_FEATURE
<222> LOCATION: (3)..(3)
<223> OTHER INFORMATION: Xaa is Glu or Glu(OtBu)
<220> FEATURE:
<221> NAME/KEY: MISC_FEATURE
<222> LOCATION: (5)..(5)
<223> OTHER INFORMATION: Xaa is Thr or Thr(tBu)
<220> FEATURE:
<221> NAME/KEY: MISC_FEATURE
<222> LOCATION: (7)..(7)
```

```
<223> OTHER INFORMATION: Xaa is Thr or Thr(tBu)
<220> FEATURE:
<221> NAME/KEY: MISC_FEATURE
<222> LOCATION: (8)..(8)
<223> OTHER INFORMATION: Xaa is Ser or Ser(tBu)
<220> FEATURE:
<221> NAME/KEY: MISC_FEATURE
<222> LOCATION: (9)..(9)
<223> OTHER INFORMATION: Xaa is Asp or Asp(OtBu)
<220> FEATURE:
<221> NAME/KEY: MISC_FEATURE
<222> LOCATION: (11)..(11)
<223> OTHER INFORMATION: Xaa is Ser or Ser(tBu)
<220> FEATURE:
<221> NAME/KEY: MISC_FEATURE
<222> LOCATION: (12)..(12)
<223> OTHER INFORMATION: Xaa is Ser(psi-z,z-pro), Ser(psi-Me,Me-pro), or
      Ser(psi-Me,Me-pro)-OH

<400> SEQUENCE: 5

Xaa Xaa Xaa Gly Xaa Phe Xaa Xaa Xaa Val Xaa Xaa
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic Fragment A (1-7)
<220> FEATURE:
<221> NAME/KEY: MISC_FEATURE
<222> LOCATION: (1)..(1)
<223> OTHER INFORMATION: Xaa is His, Boc-His, or Boc-His(Trt)
<220> FEATURE:
<221> NAME/KEY: MISC_FEATURE
<222> LOCATION: (2)..(2)
<223> OTHER INFORMATION: Xaa is Ala or Aib
<220> FEATURE:
<221> NAME/KEY: MISC_FEATURE
<222> LOCATION: (3)..(3)
<223> OTHER INFORMATION: Xaa is Glu or Glu(OtBu)
<220> FEATURE:
<221> NAME/KEY: MISC_FEATURE
<222> LOCATION: (5)..(5)
<223> OTHER INFORMATION: Xaa is Thr or Thr(tBu)
<220> FEATURE:
<221> NAME/KEY: MISC_FEATURE
<222> LOCATION: (7)..(7)
<223> OTHER INFORMATION: Xaa is Thr(psi-z,z-pro), Thr(psi-Me,Me-pro), or
      Thr(psi-Me,Me-pro)-OH

<400> SEQUENCE: 6

Xaa Xaa Xaa Gly Xaa Phe Xaa
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic fragment A (1-5)
<220> FEATURE:
<221> NAME/KEY: MISC_FEATURE
<222> LOCATION: (1)..(1)
<223> OTHER INFORMATION: Xaa is His, Boc-His, or Boc-His(Trt)
<220> FEATURE:
<221> NAME/KEY: MISC_FEATURE
<222> LOCATION: (2)..(2)
<223> OTHER INFORMATION: Xaa is Ala or Aib
<220> FEATURE:
<221> NAME/KEY: MISC_FEATURE
<222> LOCATION: (3)..(3)
<223> OTHER INFORMATION: Xaa is Glu or Glu(OtBu)
<220> FEATURE:
<221> NAME/KEY: MISC_FEATURE
```

```
<222> LOCATION: (5)..(5)
<223> OTHER INFORMATION: Xaa isThr(psi-z,z-pro), Thr(psi-Me,Me-pro), or
      Thr(psi-Me,Me-pro)-OH

<400> SEQUENCE: 7

Xaa Xaa Xaa Gly Xaa
1               5

<210> SEQ ID NO 8
<211> LENGTH: 23
<212> TYPE: PRT
<213> ORGANISM: Artificial Sequence
<220> FEATURE:
<223> OTHER INFORMATION: Synthetic fragment B (9-31)
<220> FEATURE:
<221> NAME/KEY: MISC_FEATURE
<222> LOCATION: (1)..(1)
<223> OTHER INFORMATION: Xaa is Asp or H-Asp(OtBu)
<220> FEATURE:
<221> NAME/KEY: MISC_FEATURE
<222> LOCATION: (3)..(3)
<223> OTHER INFORMATION: Xaa is Ser or Ser(tBu)
<220> FEATURE:
<221> NAME/KEY: MISC_FEATURE
<222> LOCATION: (4)..(4)
<223> OTHER INFORMATION: Xaa is Ser or Ser(tBu)
<220> FEATURE:
<221> NAME/KEY: MISC_FEATURE
<222> LOCATION: (5)..(5)
<223> OTHER INFORMATION: Xaa is Tyr or Tyr(tBu)
<220> FEATURE:
<221> NAME/KEY: MISC_FEATURE
<222> LOCATION: (7)..(7)
<223> OTHER INFORMATION: Xaa is Glu or Glu(OtBu)
<220> FEATURE:
<221> NAME/KEY: MISC_FEATURE
<222> LOCATION: (9)..(9)
<223> OTHER INFORMATION: Xaa is Gln or Gln(Trt)
<220> FEATURE:
<221> NAME/KEY: MISC_FEATURE
<222> LOCATION: (12)..(12)
<223> OTHER INFORMATION: Xaa is Lys(Pal-Glu), Lys(Pal-Glu-OtBu),
      Lys[(tBuOOC-(CH2)16-CO-gammaGlu-OtBu)-AEEA-AEEA], or
      Lys(N-(17-carboxy-1-oxoheptadecyl)-L-glutamyl-2-[2-(2-
      aminoethoxy)ethoxy]acetyl-2-[2-(2-aminoethoxy)ethoxy]acetyl)
<220> FEATURE:
<221> NAME/KEY: MISC_FEATURE
<222> LOCATION: (13)..(13)
<223> OTHER INFORMATION: Xaa is Glu or Glu(OtBu)
<220> FEATURE:
<221> NAME/KEY: MISC_FEATURE
<222> LOCATION: (17)..(17)
<223> OTHER INFORMATION: Xaa is Trp or Trp(N-in-Boc)
<220> FEATURE:
<221> NAME/KEY: MISC_FEATURE
<222> LOCATION: (20)..(20)
<223> OTHER INFORMATION: Xaa is Arg or Arg(Pbf)
<220> FEATURE:
<221> NAME/KEY: MISC_FEATURE
<222> LOCATION: (22)..(22)
<223> OTHER INFORMATION: Xaa is Arg or Arg(Pbf)
<220> FEATURE:
<221> NAME/KEY: MISC_FEATURE
<222> LOCATION: (23)..(23)
<223> OTHER INFORMATION: Xaa is Gly-resin, Gly-Wang resin, or Gly-MBH
      resin

<400> SEQUENCE: 8

Xaa Val Xaa Xaa Xaa Leu Xaa Gly Xaa Ala Ala Xaa Xaa Phe Ile Ala
1               5                   10                  15

Xaa Leu Val Xaa Gly Xaa Xaa
            20

<210> SEQ ID NO 9
```

```
<211> LENGTH: 20
<212> TYPE: PRT
<213> ORGANISM: Artificial Sequence
<220> FEATURE:
<223> OTHER INFORMATION: Synthetic fragment B (12-31)
<220> FEATURE:
<221> NAME/KEY: MISC_FEATURE
<222> LOCATION: (1)..(1)
<223> OTHER INFORMATION: Xaa is Ser or H-Ser(tBu)
<220> FEATURE:
<221> NAME/KEY: MISC_FEATURE
<222> LOCATION: (2)..(2)
<223> OTHER INFORMATION: Xaa is Tyr or Tyr(tBu)
<220> FEATURE:
<221> NAME/KEY: MISC_FEATURE
<222> LOCATION: (4)..(4)
<223> OTHER INFORMATION: Xaa is Glu or Glu(OtBu)
<220> FEATURE:
<221> NAME/KEY: MISC_FEATURE
<222> LOCATION: (6)..(6)
<223> OTHER INFORMATION: Xaa is Gln or Gln(Trt)
<220> FEATURE:
<221> NAME/KEY: MISC_FEATURE
<222> LOCATION: (9)..(9)
<223> OTHER INFORMATION: Xaa is Lys(Pal-Glu), Lys(Pal-Glu-OtBu), or
      Lys(N-(17-carboxy-1-oxoheptadecyl)-L-glutamyl-2-[2-(2-
      aminoethoxy)ethoxy]acetyl-2-[2-(2-aminoethoxy)ethoxy]acetyl)
<220> FEATURE:
<221> NAME/KEY: MISC_FEATURE
<222> LOCATION: (10)..(10)
<223> OTHER INFORMATION: Xaa is Glu or Glu(OtBu)
<220> FEATURE:
<221> NAME/KEY: MISC_FEATURE
<222> LOCATION: (14)..(14)
<223> OTHER INFORMATION: Xaa is Trp or Trp(N-in-Boc)
<220> FEATURE:
<221> NAME/KEY: MISC_FEATURE
<222> LOCATION: (17)..(17)
<223> OTHER INFORMATION: Xaa is Arg or Arg(Pbf)
<220> FEATURE:
<221> NAME/KEY: MISC_FEATURE
<222> LOCATION: (19)..(19)
<223> OTHER INFORMATION: Xaa is Arg or Arg(Pbf)
<220> FEATURE:
<221> NAME/KEY: MISC_FEATURE
<222> LOCATION: (20)..(20)
<223> OTHER INFORMATION: Xaa is Gly-resin or Gly-Wang resin

<400> SEQUENCE: 9

Xaa Xaa Leu Xaa Gly Xaa Ala Ala Xaa Xaa Phe Ile Ala Xaa Leu Val
1               5                   10                  15

Xaa Gly Xaa Xaa
            20

<210> SEQ ID NO 10
<211> LENGTH: 19
<212> TYPE: PRT
<213> ORGANISM: Artificial Sequence
<220> FEATURE:
<223> OTHER INFORMATION: Synthetic fragment B (13-31)
<220> FEATURE:
<221> NAME/KEY: MISC_FEATURE
<222> LOCATION: (1)..(1)
<223> OTHER INFORMATION: Xaa is Tyr or H-Tyr(tBu)
<220> FEATURE:
<221> NAME/KEY: MISC_FEATURE
<222> LOCATION: (3)..(3)
<223> OTHER INFORMATION: Xaa is Glu or Glu(OtBu)
<220> FEATURE:
<221> NAME/KEY: MISC_FEATURE
<222> LOCATION: (5)..(5)
<223> OTHER INFORMATION: Xaa is Gln or Gln(Trt)
<220> FEATURE:
<221> NAME/KEY: MISC_FEATURE
<222> LOCATION: (8)..(8)
<223> OTHER INFORMATION: Xaa is Lys(Pal-Glu), Lys(Pal-Glu-OtBu), or
```

```
      Lys(N-(17-carboxy-1-oxoheptadecyl)-L-glutamyl-2-[2-(2-
      aminoethoxy)ethoxy]acetyl-2-[2-(2-aminoethoxy)ethoxy]acetyl)
<220> FEATURE:
<221> NAME/KEY: MISC_FEATURE
<222> LOCATION: (9)..(9)
<223> OTHER INFORMATION: Xaa is Glu or Glu(OtBu)
<220> FEATURE:
<221> NAME/KEY: MISC_FEATURE
<222> LOCATION: (13)..(13)
<223> OTHER INFORMATION: Xaa is Trp or Trp(N-in-Boc)
<220> FEATURE:
<221> NAME/KEY: MISC_FEATURE
<222> LOCATION: (16)..(16)
<223> OTHER INFORMATION: Xaa is Arg or Arg(Pbf)
<220> FEATURE:
<221> NAME/KEY: MISC_FEATURE
<222> LOCATION: (18)..(18)
<223> OTHER INFORMATION: Xaa is Arg or Arg(Pbf)
<220> FEATURE:
<221> NAME/KEY: MISC_FEATURE
<222> LOCATION: (19)..(19)
<223> OTHER INFORMATION: Xaa is Gly-resin or Gly-Wang resin

<400> SEQUENCE: 10

Xaa Leu Xaa Gly Xaa Ala Ala Xaa Xaa Phe Ile Ala Xaa Leu Val Xaa
1               5                   10                  15

Gly Xaa Xaa

<210> SEQ ID NO 11
<211> LENGTH: 24
<212> TYPE: PRT
<213> ORGANISM: Artificial Sequence
<220> FEATURE:
<223> OTHER INFORMATION: Synthetic fragment B (8-31)
<220> FEATURE:
<221> NAME/KEY: MISC_FEATURE
<222> LOCATION: (1)..(1)
<223> OTHER INFORMATION: Xaa is Ser or H-Ser(tBu)
<220> FEATURE:
<221> NAME/KEY: MISC_FEATURE
<222> LOCATION: (2)..(2)
<223> OTHER INFORMATION: Xaa is Asp or Asp(OtBu)
<220> FEATURE:
<221> NAME/KEY: MISC_FEATURE
<222> LOCATION: (4)..(4)
<223> OTHER INFORMATION: Xaa is Ser or Ser(tBu)
<220> FEATURE:
<221> NAME/KEY: MISC_FEATURE
<222> LOCATION: (5)..(5)
<223> OTHER INFORMATION: Xaa is Ser or Ser(tBu)
<220> FEATURE:
<221> NAME/KEY: MISC_FEATURE
<222> LOCATION: (6)..(6)
<223> OTHER INFORMATION: Xaa is Tyr or Tyr(tBu)
<220> FEATURE:
<221> NAME/KEY: MISC_FEATURE
<222> LOCATION: (8)..(8)
<223> OTHER INFORMATION: Xaa is Glu or Glu(OtBu)
<220> FEATURE:
<221> NAME/KEY: MISC_FEATURE
<222> LOCATION: (10)..(10)
<223> OTHER INFORMATION: Xaa is Gln or Gln(Trt)
<220> FEATURE:
<221> NAME/KEY: MISC_FEATURE
<222> LOCATION: (13)..(13)
<223> OTHER INFORMATION: Xaa is Lys(Pal-Glu), Lys(Pal-Glu-OtBu), or
      Lys(N-(17-carboxy-1-oxoheptadecyl)-L-glutamyl-2-[2-(2-
      aminoethoxy)ethoxy]acetyl-2-[2-(2-aminoethoxy)ethoxy]acetyl)
<220> FEATURE:
<221> NAME/KEY: MISC_FEATURE
<222> LOCATION: (14)..(14)
<223> OTHER INFORMATION: Xaa is Glu or Glu(OtBu)
<220> FEATURE:
<221> NAME/KEY: MISC_FEATURE
<222> LOCATION: (18)..(18)
<223> OTHER INFORMATION: Xaa is Trp or Trp(N-in-Boc)
```

```
<220> FEATURE:
<221> NAME/KEY: MISC_FEATURE
<222> LOCATION: (21)..(21)
<223> OTHER INFORMATION: Xaa is Arg or Arg(Pbf)
<220> FEATURE:
<221> NAME/KEY: MISC_FEATURE
<222> LOCATION: (23)..(23)
<223> OTHER INFORMATION: Xaa is Arg or Arg(Pbf)
<220> FEATURE:
<221> NAME/KEY: MISC_FEATURE
<222> LOCATION: (24)..(24)
<223> OTHER INFORMATION: Xaa is Gly-resin or Gly-Wang resin

<400> SEQUENCE: 11

Xaa Xaa Val Xaa Xaa Xaa Leu Xaa Gly Xaa Ala Ala Xaa Xaa Phe Ile
1               5                   10                  15

Ala Xaa Leu Val Xaa Gly Xaa Xaa
            20

<210> SEQ ID NO 12
<211> LENGTH: 26
<212> TYPE: PRT
<213> ORGANISM: Artificial Sequence
<220> FEATURE:
<223> OTHER INFORMATION: Synthetic fragment B (6-31)
<220> FEATURE:
<221> NAME/KEY: MISC_FEATURE
<222> LOCATION: (1)..(1)
<223> OTHER INFORMATION: Xaa is Phe or H-Phe
<220> FEATURE:
<221> NAME/KEY: MISC_FEATURE
<222> LOCATION: (2)..(2)
<223> OTHER INFORMATION: Xaa is Thr or Thr(tBu)
<220> FEATURE:
<221> NAME/KEY: MISC_FEATURE
<222> LOCATION: (3)..(3)
<223> OTHER INFORMATION: Xaa is Ser or Ser(tBu)
<220> FEATURE:
<221> NAME/KEY: MISC_FEATURE
<222> LOCATION: (4)..(4)
<223> OTHER INFORMATION: Xaa is Asp or Asp(OtBu)
<220> FEATURE:
<221> NAME/KEY: MISC_FEATURE
<222> LOCATION: (6)..(6)
<223> OTHER INFORMATION: Xaa is Ser or Ser(tBu)
<220> FEATURE:
<221> NAME/KEY: MISC_FEATURE
<222> LOCATION: (7)..(7)
<223> OTHER INFORMATION: Xaa is Ser or Ser(tBu)
<220> FEATURE:
<221> NAME/KEY: MISC_FEATURE
<222> LOCATION: (8)..(8)
<223> OTHER INFORMATION: Xaa is Tyr or Tyr(tBu)
<220> FEATURE:
<221> NAME/KEY: MISC_FEATURE
<222> LOCATION: (10)..(10)
<223> OTHER INFORMATION: Xaa is Glu or Glu(OtBu)
<220> FEATURE:
<221> NAME/KEY: MISC_FEATURE
<222> LOCATION: (12)..(12)
<223> OTHER INFORMATION: Xaa is Gln or Gln(Trt)
<220> FEATURE:
<221> NAME/KEY: MISC_FEATURE
<222> LOCATION: (15)..(15)
<223> OTHER INFORMATION: Xaa is Lys(Pal-Glu), Lys(Pal-Glu-OtBu), or
      Lys(N-(17-carboxy-1-oxoheptadecyl)-L-glutamyl-2-[2-(2-
      aminoethoxy)ethoxy]acetyl-2-[2-(2-aminoethoxy)ethoxy]acetyl)
<220> FEATURE:
<221> NAME/KEY: MISC_FEATURE
<222> LOCATION: (16)..(16)
<223> OTHER INFORMATION: Xaa is Glu or Glu(OtBu)
<220> FEATURE:
<221> NAME/KEY: MISC_FEATURE
<222> LOCATION: (20)..(20)
<223> OTHER INFORMATION: Xaa is Trp or Trp(N-in-Boc)
<220> FEATURE:
```

```
<221> NAME/KEY: MISC_FEATURE
<222> LOCATION: (23)..(23)
<223> OTHER INFORMATION: Xaa is Arg or Arg(Pbf)
<220> FEATURE:
<221> NAME/KEY: MISC_FEATURE
<222> LOCATION: (25)..(25)
<223> OTHER INFORMATION: Xaa is Arg or Arg(Pbf)
<220> FEATURE:
<221> NAME/KEY: MISC_FEATURE
<222> LOCATION: (26)..(26)
<223> OTHER INFORMATION: Xaa is Gly-resin or Gly-Wang resin

<400> SEQUENCE: 12

Xaa Xaa Xaa Xaa Val Xaa Xaa Xaa Leu Xaa Gly Xaa Ala Ala Xaa Xaa
1               5                   10                  15

Phe Ile Ala Xaa Leu Val Xaa Gly Xaa Xaa
            20                  25

<210> SEQ ID NO 13
<211> LENGTH: 15
<212> TYPE: PRT
<213> ORGANISM: Artificial Sequence
<220> FEATURE:
<223> OTHER INFORMATION: Synthetic fragment D (17-31)
<220> FEATURE:
<221> NAME/KEY: MISC_FEATURE
<222> LOCATION: (1)..(1)
<223> OTHER INFORMATION: Xaa is Gln, H-Gln, or H-Gln(Trt)
<220> FEATURE:
<221> NAME/KEY: MISC_FEATURE
<222> LOCATION: (4)..(4)
<223> OTHER INFORMATION: Xaa is Lys(Pal-Glu), Lys(Pal-Glu-OtBu),
      Lys[(tBuOOC-(CH2)16-CO-gammaGlu-OtBu)-AEEA-AEEA], or
      Lys(N-(17-carboxy-1-oxoheptadecyl)-L-glutamyl-2-[2-(2-
      aminoethoxy)ethoxy]acetyl-2-[2-(2-aminoethoxy)ethoxy]acetyl)
<220> FEATURE:
<221> NAME/KEY: MISC_FEATURE
<222> LOCATION: (5)..(5)
<223> OTHER INFORMATION: Xaa is Glu or Glu(OtBu)
<220> FEATURE:
<221> NAME/KEY: MISC_FEATURE
<222> LOCATION: (9)..(9)
<223> OTHER INFORMATION: Xaa is Trp or Trp(N-in-Boc)
<220> FEATURE:
<221> NAME/KEY: MISC_FEATURE
<222> LOCATION: (12)..(12)
<223> OTHER INFORMATION: Xaa is Arg or Arg(Pbf)
<220> FEATURE:
<221> NAME/KEY: MISC_FEATURE
<222> LOCATION: (14)..(14)
<223> OTHER INFORMATION: Xaa is Arg or Arg(Pbf)
<220> FEATURE:
<221> NAME/KEY: MISC_FEATURE
<222> LOCATION: (15)..(15)
<223> OTHER INFORMATION: Xaa is Gly-resin, Gly-Wang resin, or Gly-O-MBH
      Resin

<400> SEQUENCE: 13

Xaa Ala Ala Xaa Xaa Phe Ile Ala Xaa Leu Val Xaa Gly Xaa Xaa
1               5                   10                  15

<210> SEQ ID NO 14
<211> LENGTH: 8
<212> TYPE: PRT
<213> ORGANISM: Artificial Sequence
<220> FEATURE:
<223> OTHER INFORMATION: Synthetic fragment C (9-16)
<220> FEATURE:
<221> NAME/KEY: MISC_FEATURE
<222> LOCATION: (1)..(1)
<223> OTHER INFORMATION: Xaa is Asp or Fmoc-Asp(OtBu)
<220> FEATURE:
<221> NAME/KEY: MISC_FEATURE
<222> LOCATION: (3)..(3)
```

```
<223> OTHER INFORMATION: Xaa is Ser or Ser(tBu)
<220> FEATURE:
<221> NAME/KEY: MISC_FEATURE
<222> LOCATION: (4)..(4)
<223> OTHER INFORMATION: Xaa is Ser or Ser(tBu)
<220> FEATURE:
<221> NAME/KEY: MISC_FEATURE
<222> LOCATION: (5)..(5)
<223> OTHER INFORMATION: Xaa is Tyr or Tyr(tBu)
<220> FEATURE:
<221> NAME/KEY: MISC_FEATURE
<222> LOCATION: (7)..(7)
<223> OTHER INFORMATION: Xaa is Glu or Glu(OtBu)
<220> FEATURE:
<221> NAME/KEY: MISC_FEATURE
<222> LOCATION: (8)..(8)
<223> OTHER INFORMATION: Xaa is Gly or Gly-OH

<400> SEQUENCE: 14

Xaa Val Xaa Xaa Xaa Leu Xaa Xaa
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Fragment C (12-16)
<220> FEATURE:
<221> NAME/KEY: MISC_FEATURE
<222> LOCATION: (1)..(1)
<223> OTHER INFORMATION: Xaa is Ser or Fmoc-Ser(tBu)
<220> FEATURE:
<221> NAME/KEY: MISC_FEATURE
<222> LOCATION: (2)..(2)
<223> OTHER INFORMATION: Xaa is Tyr or Tyr(tBu)
<220> FEATURE:
<221> NAME/KEY: MISC_FEATURE
<222> LOCATION: (4)..(4)
<223> OTHER INFORMATION: Xaa is Glu or Glu(OtBu)
<220> FEATURE:
<221> NAME/KEY: MISC_FEATURE
<222> LOCATION: (5)..(5)
<223> OTHER INFORMATION: Xaa is Gly or Gly-OH

<400> SEQUENCE: 15

Xaa Xaa Leu Xaa Xaa
1               5

<210> SEQ ID NO 16
<211> LENGTH: 4
<212> TYPE: PRT
<213> ORGANISM: Artificial Sequence
<220> FEATURE:
<223> OTHER INFORMATION: Synthetic fragment C (13-16)
<220> FEATURE:
<221> NAME/KEY: MISC_FEATURE
<222> LOCATION: (1)..(1)
<223> OTHER INFORMATION: Xaa is Tyr or Fmoc-Tyr(tBu)
<220> FEATURE:
<221> NAME/KEY: MISC_FEATURE
<222> LOCATION: (3)..(3)
<223> OTHER INFORMATION: Xaa is Glu or Glu(OtBu)
<220> FEATURE:
<221> NAME/KEY: MISC_FEATURE
<222> LOCATION: (4)..(4)
<223> OTHER INFORMATION: Xaa is Gly or Gly-OH

<400> SEQUENCE: 16

Xaa Leu Xaa Xaa
1

<210> SEQ ID NO 17
```

```
<211> LENGTH: 9
<212> TYPE: PRT
<213> ORGANISM: Artificial Sequence
<220> FEATURE:
<223> OTHER INFORMATION: Synthetic fragment C (8-16)
<220> FEATURE:
<221> NAME/KEY: MISC_FEATURE
<222> LOCATION: (1)..(1)
<223> OTHER INFORMATION: Xaa is Ser or Fmoc-Ser(tBu)
<220> FEATURE:
<221> NAME/KEY: MISC_FEATURE
<222> LOCATION: (2)..(2)
<223> OTHER INFORMATION: Xaa is Asp or Asp(OtBu)
<220> FEATURE:
<221> NAME/KEY: MISC_FEATURE
<222> LOCATION: (4)..(4)
<223> OTHER INFORMATION: Xaa is Ser or Ser(tBu)
<220> FEATURE:
<221> NAME/KEY: MISC_FEATURE
<222> LOCATION: (5)..(5)
<223> OTHER INFORMATION: Xaa is Ser or Ser(tBu)
<220> FEATURE:
<221> NAME/KEY: MISC_FEATURE
<222> LOCATION: (6)..(6)
<223> OTHER INFORMATION: Xaa is Tyr or Tyr(tBu)
<220> FEATURE:
<221> NAME/KEY: MISC_FEATURE
<222> LOCATION: (8)..(8)
<223> OTHER INFORMATION: Xaa is Glu or Glu(OtBu)
<220> FEATURE:
<221> NAME/KEY: MISC_FEATURE
<222> LOCATION: (9)..(9)
<223> OTHER INFORMATION: Xaa is Gly or Gly-OH

<400> SEQUENCE: 17

Xaa Xaa Val Xaa Xaa Xaa Leu Xaa Xaa
1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic fragment C (6-16)
<220> FEATURE:
<221> NAME/KEY: MISC_FEATURE
<222> LOCATION: (1)..(1)
<223> OTHER INFORMATION: Xaa is Phe or Fmoc-Phe
<220> FEATURE:
<221> NAME/KEY: MISC_FEATURE
<222> LOCATION: (2)..(2)
<223> OTHER INFORMATION: Xaa is Thr or Thr(tBu)
<220> FEATURE:
<221> NAME/KEY: MISC_FEATURE
<222> LOCATION: (3)..(3)
<223> OTHER INFORMATION: Xaa is Ser or Ser(tBu)
<220> FEATURE:
<221> NAME/KEY: MISC_FEATURE
<222> LOCATION: (4)..(4)
<223> OTHER INFORMATION: Xaa is Asp or Asp(OtBu)
<220> FEATURE:
<221> NAME/KEY: MISC_FEATURE
<222> LOCATION: (6)..(6)
<223> OTHER INFORMATION: Xaa is Ser or Ser(tBu)
<220> FEATURE:
<221> NAME/KEY: MISC_FEATURE
<222> LOCATION: (7)..(7)
<223> OTHER INFORMATION: Xaa is Ser or Ser(tBu)
<220> FEATURE:
<221> NAME/KEY: MISC_FEATURE
<222> LOCATION: (8)..(8)
<223> OTHER INFORMATION: Xaa is Tyr or Tyr(tBu)
<220> FEATURE:
<221> NAME/KEY: MISC_FEATURE
<222> LOCATION: (9)..(9)
<223> OTHER INFORMATION: Xaa is Gly or Gly-OH
<220> FEATURE:
```

```
<221> NAME/KEY: MISC_FEATURE
<222> LOCATION: (10)..(10)
<223> OTHER INFORMATION: Xaa is Glu or Glu(OtBu)
<220> FEATURE:
<221> NAME/KEY: MISC_FEATURE
<222> LOCATION: (11)..(11)
<223> OTHER INFORMATION: Xaa is Gly or Gly-OH

<400> SEQUENCE: 18

Xaa Xaa Xaa Xaa Val Xaa Xaa Xaa Leu Xaa Xaa
1               5                   10

<210> SEQ ID NO 19
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Ala or Aib
<220> FEATURE:
<221> NAME/KEY: MISC_FEATURE
<222> LOCATION: (20)..(20)
<223> OTHER INFORMATION: Xaa is Lys(Pal-Glu) or
     Lys(N-(17-carboxy-1-oxoheptadecyl)-L-glutamyl-2-[2-(2-
     aminoethoxy)ethoxy]acetyl-2-[2-(2-aminoethoxy)ethoxy]acetyl)

<400> SEQUENCE: 19

His Xaa Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg Gly
            20                  25                  30

<210> SEQ ID NO 20
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Asp or H-Asp(OtBu)
<220> FEATURE:
<221> NAME/KEY: MISC_FEATURE
<222> LOCATION: (3)..(3)
<223> OTHER INFORMATION: Xaa is Ser or Ser(tBu)
<220> FEATURE:
<221> NAME/KEY: MISC_FEATURE
<222> LOCATION: (4)..(4)
<223> OTHER INFORMATION: Xaa is Ser or Ser(tBu)
<220> FEATURE:
<221> NAME/KEY: MISC_FEATURE
<222> LOCATION: (5)..(5)
<223> OTHER INFORMATION: Xaa is Tyr or Tyr(tBu)
<220> FEATURE:
<221> NAME/KEY: MISC_FEATURE
<222> LOCATION: (7)..(7)
<223> OTHER INFORMATION: Xaa is Glu or Glu(OtBu)
<220> FEATURE:
<221> NAME/KEY: MISC_FEATURE
<222> LOCATION: (9)..(9)
<223> OTHER INFORMATION: Xaa is Gln or Gln(Trt)
<220> FEATURE:
<221> NAME/KEY: MISC_FEATURE
<222> LOCATION: (12)..(12)
<223> OTHER INFORMATION: Xaa is Lys(Pal-Glu), Lys(Pal-Glu-OtBu),
     Lys[(tBuOOC-(CH2)16-CO-gammaGlu-OtBu)-AEEA-AEEA], or
     Lys(N-(17-carboxy-1-oxoheptadecyl)-L-glutamyl-2-[2-(2-
     aminoethoxy)ethoxy]acetyl-2-[2-(2-aminoethoxy)ethoxy]acetyl)
<220> FEATURE:
<221> NAME/KEY: MISC_FEATURE
```

```
<222> LOCATION: (13)..(13)
<223> OTHER INFORMATION: Xaa is Glu or Glu(OtBu)
<220> FEATURE:
<221> NAME/KEY: MISC_FEATURE
<222> LOCATION: (17)..(17)
<223> OTHER INFORMATION: Xaa is Trp or Trp(N-in-Boc)
<220> FEATURE:
<221> NAME/KEY: MISC_FEATURE
<222> LOCATION: (20)..(20)
<223> OTHER INFORMATION: Xaa is Arg or Arg(Pbf)
<220> FEATURE:
<221> NAME/KEY: MISC_FEATURE
<222> LOCATION: (22)..(22)
<223> OTHER INFORMATION: Xaa is Arg or Arg(Pbf)
<220> FEATURE:
<221> NAME/KEY: MISC_FEATURE
<222> LOCATION: (23)..(23)
<223> OTHER INFORMATION: Xaa is Gly-Wang resin, or Gly-O-MBH Resin

<400> SEQUENCE: 20

Xaa Val Xaa Xaa Xaa Leu Xaa Gly Xaa Ala Ala Xaa Xaa Phe Ile Ala
1               5                   10                  15

Xaa Leu Val Xaa Gly Xaa Xaa
                20
```

PROCESS FOR THE MANUFACTURE OF GLP-1 ANALOGUES

CROSS-REFERENCE TO RELATED APPLICATIONS

This patent application is the U.S. national phase of International Application No. PCT/EP2019/077367, filed on Oct. 9, 2019, which claims the benefit of European Patent Application No. 18199401.3, filed Oct. 9, 2018, the disclosures of which are incorporated herein by reference in their entireties for all purposes.

INCORPORATION BY REFERENCE OF MATERIAL SUBMITTED ELECTRONICALLY

Incorporated by reference in its entirety herein is a computer-readable nucleotide/amino acid sequence listing submitted concurrently herewith and identified as follows: One 18,934 bytes ASCII (Text) file named "753327-2_ST25", created on Dec. 19, 2021.

FIELD OF THE INVENTION

The present invention relates to peptide synthesis. In particular, it relates to processes for the manufacture of GLP-1 analogues. More in particular, the present invention relates to a process for the manufacture of liraglutide and semaglutide by peptide fragment condensation.

BACKGROUND OF THE INVENTION

Glucagon-like peptide-1 (GLP-1) is a naturally occurring peptide hormone with one of the most potent insulinotropic activities. GLP-1 is part of a longer peptide produced and processed to GLP-1 in the pancreas and the intestine. Glucagon-like peptide 1 (GLP-1) receptor agonists, or GLP-1 analogues, are a relatively new group of injectable drugs for the treatment of type 2 diabetes. One of their advantages over older insulin secretagogues, such as sulfonylureas or meglitinides, is that they have a lower risk of causing hypoglycemia.

Liraglutide and semaglutide are both highly similar peptides of a length of 30 amino acids, which just differ in the amino acid in position 2 (aa$^2$, which is alanine, Ala, in liraglutide and α-aminoisobutyric acid, Aib, in semaglutide) and in the side chain attached to the lysine in position 20 (Lys$^{20}$), i.e. the lipophilic albumin binding moiety. Attached to the ε-amino group of such lysine, liraglutide has a Glu-spaced palmitic acid (indicated as Pal-Glu), while semaglutide bears an octadecandioic-acylated-glutamic acid plus a further spacer.

Liraglutide and semaglutide are represented by using the "three letter code" for amino acids/peptides, according to the following:

```
                                          (SEQ ID No 19)
   1               5                10
   His-X1-Glu-Gly-Thr-Phe-Thr-Ser-Asp-Val-Ser- 15                20
   Ser-Tyr-Leu-Glu-Gly-Gln-Ala-Ala-Lys(X2)-

25        30        31
   Glu-Phe-Ile-Ala-Trp-Leu-Val-Arg-Gly-Arg-Gly
``` wherein the numbering of aminoacidic residues starts with 1, indicating N-terminal histidine, and finishes with 31, indicating C-terminal glycine, and wherein in liraglutide (SEQ ID No 1)

$X_1$ is Ala and $X_2$ is N-(1-oxohexadecyl)-L-γ-glutamyl (also indicated as Pal-Glu), depicted herebelow

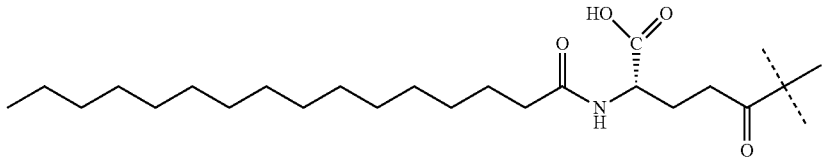

and in semaglutide (SEQ ID No 2)

$X_1$ is Aib (α-aminoisobutyric acid) and $X_2$ is N-(17-carboxy-1-oxoheptadecyl)-L-γ-glutamyl-2-[2-(2-aminoethoxy)ethoxy]acetyl-2-[2-(2-aminoethoxy)ethoxy]acetyl, depicted herebelow

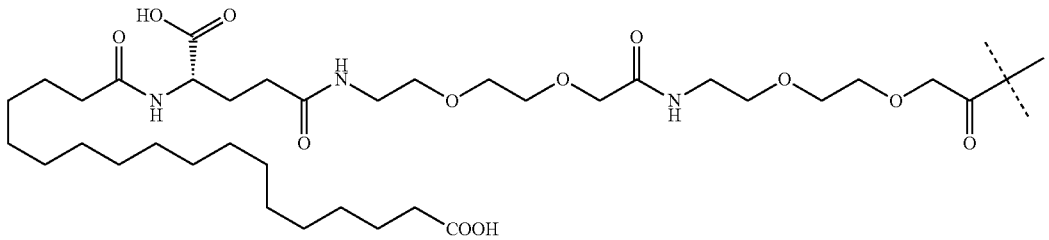

and wherein $X_2$ is attached to the ε-amino group of Lys$^{20}$ through amide bond where indicated by ⇠.

Alternatively, the two above peptides, or any fragments thereof, are represented throughout the present application by using the "one letter code" for amino acids/peptides, according to formula I:

```
                                      (SEQ ID No 19)
HX₁EGTFTSDVSSYLEGQAAK(X₂)EFIAWLVRGRG
(I)
``` wherein X₁ and X₂ are as defined above, respectively.

In a further option, the two above peptides, or any fragments thereof, are represented throughout the present application by using their chemical structure.

Fragments will herein below also be referred to by their according positions in the above mentioned sequence. For example a "fragment (1-16)" refers to the peptide sequence consisting of the amino acids present in the above sequence at positions 1 to 16.

The preparation of GLP-1 analogues has been described in several patent applications. Both sequential SPPS (Solid Phase Peptide Synthesis) and fragment based approaches were pursued.

It is worth pointing out that the branched structure of liraglutide and semaglutide and their low aqueous solubility dramatically hamper their synthesis and purification.

In a fragment based peptide synthesis, the C-terminal carboxylic group of one of the two reacting fragments has to be activated prior to coupling. The activation of C-terminal carboxylic groups of peptide fragments may however lead to both activated ester and oxazolone formation, which can be easily racemized in the basic conditions during coupling (N. L. Benoiton. Chemistry of Peptide Synthesis. Tailor and Francis Group. 2006). Therefore, the crude peptides obtained this way contain impurities corresponding to the isomerized product. Since the isomeric impurities have very similar retention times as the required target peptide, it is very difficult to separate these impurities from said peptide. One way to tackle this issue was to split GLP-1 analogues peptide sequence at Gly⁴ and/or Gly¹⁶ positions and couple the fragments in a final step (as disclosed, for instance in CN104004083 and in WO2016046753).

However, the extremely low solubility of the protected fragment (1-16) in the solvents commonly used in peptide synthesis makes the final coupling with the scheme fragment (1-16)+ fragment (17-31) very difficult, especially when the C-terminal fragment (i.e. fragment (17-31)) is immobilized on a solid support.

In addition, long peptides like liraglutide and semaglutide are prone to intermolecular aggregation of peptide chains. This problem, together with intramolecular peptide folding, is particularly serious during peptide synthesis, decreasing the efficiency of the amino acid couplings and deprotections, leading to the formation of many side products or even to the impossibility to obtain the target peptide.

The need to develop an efficient, simple and industrially viable process of preparing liraglutide and semaglutide is therefore still existent. An improved process to overcome the synthesis issues not solved by prior art and to provide both peptides in high yield and with a favorable impurity profile is thus very much desirable.

Herein described is a new and improved solid phase synthesis of liraglutide and semaglutide which makes use of a convergent approach involving a final fragment coupling step, wherein the N-terminal fragment A has a pseudoproline at the C-terminal reactive site, according to the general Scheme 1:

fragment A-pseudoproline-COOH + NH₂-fragment B-solid support

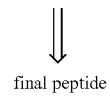

final peptide

In particular, a strategy is devised, wherein the protected N-terminal pseudoproline fragment (or fragment A) is prepared by SPPS and then cleaved from the solid support, while keeping α-amino group and side-chains protections, and the solid supported C-terminal fragment (or fragment B) is prepared by SPPS or CSPPS (convergent SPPS) and only its α-amino group is deprotected before final fragment coupling. The complete sequenced peptide is finally cleaved from solid support and deprotected, and optionally purified to obtain pure liraglutide or semaglutide, respectively. It was surprisingly found that, the use of pseudoproline at the C-terminal end in the present fragment-based approach effectively reduces the formation of impurities so that the obtained crude peptide can be more easily purified to give the final peptide in a high total yield.

OBJECT OF THE INVENTION

It is an object of the present invention to provide an improved process in solid phase for the preparation of GLP-1 analogues, or a pharmaceutically acceptable salt thereof, which results in the crude peptides in a high yield and a good impurity profile, facilitating final purification.

It is another object of the present invention to provide an efficient, simple and industrially viable process of preparing liraglutide and semaglutide.

It is a further object of the present invention to provide a process of preparing liraglutide and semaglutide with higher yield and purity than achieved in the state of the art.

It is a further object of the present invention to provide useful peptide intermediates for the synthesis of liraglutide or semaglutide, or a pharmaceutically acceptable salt thereof.

SUMMARY OF THE INVENTION

The present invention provides a convergent method for the preparation of some GLP-1 analogues in solid phase synthesis, which comprises the final step of coupling a first N-terminal protected peptide fragment characterised by having a pseudoproline at the C-terminal reactive site (protected N-terminal pseudoproline fragment A), with a second protected C-terminal peptide fragment (fragment B) attached to a solid support.

Fragment A has a C-terminal pseudoproline reactive site and is protected at its N-terminal α-amino group. Fragment A is preferably protected at its amino acids side-chains.

Fragment A is selected from the group consisting of:

```
His-X₁-Glu-Gly-Thr-Phe-Thr-Ser(ψ^{r,r}pro)
(SEQ ID No 3), also referred to as
fragment A (1-8), His-X₁-Glu-Gly-Thr-Phe-Thr-Ser-Asp- Val-Ser(ψ^{r,r}pro)
(SEQ ID No 4), also referred to as
fragment A (1-11),
```

```
His-X₁-Glu-Gly-Thr-Phe-Thr-Ser-Asp-Val-

Ser-Ser(ψ^(z,z)pro)
(SEQ ID NO 6), also referred to as
fragment A (1-7),

His-X₁-Glu-Gly-Thr-Phe-Thr(ψ^(z,z)pro)
(SEQ ID No 5), also referred to as
fragment A (1-12),
and His-X₁-Glu-Gly-Thr(ψ^(z,z)pro)
(SEQ ID No 7), referred to as
fragment A (1-5),
``` wherein $X_1$ is Ala for liraglutide and Aib for semaglutide, and wherein aa($\psi^{z,z}$pro) indicates that the C-terminal amino acid (aa), preferably Ser or Thr, is pseudoproline protected, according to the following formula:

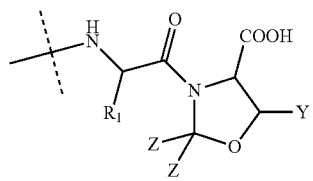

wherein

Y is hydrogen for Ser and methyl (Me) for Thr,

Z is hydrogen or methyl (Me), and $R_1$ is the side-chain of the amino acid beside the pseudoproline protected amino acid.

The fragment number notation in brackets, for instance (1-8), merely indicates the position of the fragment with regard to the full peptide sequence.

Therefore, for instance, aa-Ser($\psi^{Me,Me}$pro) indicates

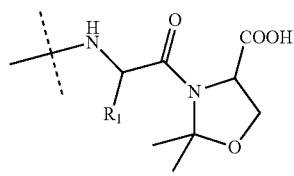

wherein $R_1$ is the side-chain of aa, and Thr-Ser($\psi^{z,z}$pro) in fragment A (1-8) as defined above indicates:

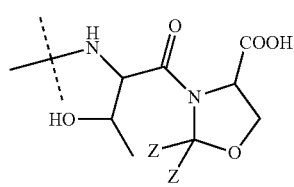

wherein Z is as defined above.

Stereochemistry is not defined in the above structures for simplicity. L-amino acids are always used if not otherwise indicated.

Fragment B is bound to a resin, or solid support, at its C-terminal amino acid, i.e. glycine 31 ($Gly^{31}$). The solid support is preferably selected from Wang resin, 2-chlorotrityl chloride (CTC) resin, trityl chloride resin, MBH and 4-MeO-MBH resin. The solid support is more preferably selected from Wang resin, 2-chlorotrityl chloride (CTC) resin and trityl chloride resin. Fragment B is preferably protected at its amino acids side-chains, including $X_2$ moiety of $Lys^{20}$.

Fragment B is selected from the group consisting of

```
Asp-Val-Ser-Ser-Tyr-Leu-Glu-Gly-

Gln-Ala-Ala-Lys(X₂)-Glu-Phe-Ile-Ala-

-Trp-Leu-Val-Arg-Gly-Arg-Gly-resin
(SEQ ID No 8), also referred to as
fragment B (9-31), Ser-Tyr-Leu-Glu-Gly-Gln-Ala-Ala-Lys(X₂)-

Glu-Phe-Ile-Ala-Trp-Leu-Val-Arg-Gly-Arg-

Gly-resin
(SEQ ID No 9), also referred to as
fragment B (12-31),

Tyr-Leu-Glu-Gly-Gln-Ala-Ala-Lys(X₂)-Glu-

Phe-Ile-Ala-Trp-Leu-Val-Arg-Gly-Arg-

Gly-resin
(SEQ ID No 10), also referred to as
fragment B (13-31),

Ser-Asp-Val-Ser-Ser-Tyr-Leu-Glu-Gly-

Gln-Ala-Ala-Lys(X₂)-Glu-Phe-Ile-Ala-

-Trp-Leu-Val-Arg-Gly-Arg-Gly-resin
(SEQ ID No 11), also referred to as
fragment B (8-31),
and Phe-Thr-Ser-Asp-Val-Ser-Ser-Tyr-Leu-Glu- Gly-Gln-Ala-Ala-Lys(X₂)-Glu-Phe-Ile-Ala- -Trp-Leu-Val-Arg-Gly-Arg-Gly-resin
(SEQ ID No 12), also referred to as
fragment B (6-31),
``` wherein $X_2$ is N-(1-oxohexadecyl)-L-γ-glutamyl (Pal-Glu) for liraglutide, and $X_2$ is N-(17-carboxy-1-oxoheptadecyl)-L-γ-glutamyl-2-[2-(2-aminoethoxy)ethoxy]acetyl-2-[2-(2-aminoethoxy)ethoxy]acetyl for semaglutide, optionally protected.

Fragment A and fragment B are coupled, so that either liraglutide or semaglutide full sequence is obtained. The obtained 30-aa peptide, preferably side-chain protected, is then deprotected and/or cleaved from the solid support to obtain the crude peptide. Such crude peptide is optionally purified to obtain pure liraglutide or semaglutide. The method of present invention provides liraglutide and semaglutide in a high yield and a high purity.

Moreover, the present invention provides the intermediate fragments A and B and methods for their preparation.

DETAILED DESCRIPTION OF THE INVENTION

The present invention discloses a novel method for preparing a GLP-1 analogue with high yield and purity. In particular, it consists of a convergent approach on the solid phase. More in particular, the final coupling involves a peptide fragment (fragment A) characterised by having a pseudoproline at the C-terminal reactive site.

Pseudoprolines were developed by Mutter in 1992 (T. Haack, M. Mutter, Serine derived oxazolidines as secondary structure disrupting, solubilizing building blocks in peptide synthesis, Tetrahedron Lett. 1992, 33, 1589-1592). Surprisingly, the use of pseudoproline at the C-terminal end in the present fragment-based approach has been found to effectively reduce the amount of impurities formed, thus leading to the improved process which is object of the present invention. Such method substantially reduces the formation of impurities so that the obtained crude peptide can be easily purified to give the final peptide in a high total yield.

In a further aspect, the present invention provides the required peptide fragments A and B and the method of preparing these. Such synthesis is performed either by standard SPPS or by CSPPS, both by using a coupling reagent system.

The term "peptide fragment" or "fragment", describes a peptide with a partial amino acid sequence, with reference to liraglutide or semaglutide sequence. It can be optionally attached to a resin at its C-terminal amino acid. A peptide fragment can be protected or not protected. A peptide fragment can have a pseudoproline at its C-terminal end, or at an internal position in the aminoacidic sequence.

The term "protected peptide fragment" or "protected fragment" describes a peptide fragment which can independently bear protecting groups at its amino acids side-chains, or side groups, and/or at its α-amino group.

A fragment, or peptide fragment, can be also indicated with a specific amino acids sequence, like $aa^1$-$aa^2$- ... -$aa^n$ wherein $aa^x$ is the three letter code of the amino acid in position x, and wherein the presence or not of protecting groups, either on the side-chains or on α-amino group, is undefined. The necessity of protecting side chains of amino acids during peptide synthesis under certain conditions is known in the art and various strategies to identify suitable protection strategies have been described.

If in this description for a specific amino acid sequence (fragment) protective groups of the side chains are specifically mentioned in brackets accompanying the three letter code of the amino acid it is understood that the remaining amino acids which are represented with a plain three letter code are unprotected.

When the fragment is indicated with $aa^1$-$aa^2$- ... -$aa^n$-OH it is intended that the C-terminal amino acid $aa^n$ has a free carboxylic acid.

When the fragment is indicated with

H-$aa^1$-$aa^2$- ... -$aa^n$ it is intended that the N-terminal amino acid $aa^1$ has a free α-amino group.

When the fragment is indicated with $aa^1$-$aa^2$- ... -$aa^n(\psi^{z,z}$pro)-OH it is intended that the C-terminal amino acid $aa^n$ is pseudoproline protected and has a free carboxylic acid, according to the following structure:

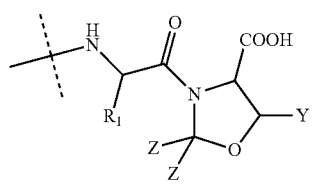

wherein $R_1$ is the side-chain of $aa^{(n-1)}$, and $aa^n(\psi^{z,z}$pro)-OH can be Ser($\psi^{z,z}$pro)-OH, wherein Y is hydrogen, and Z is hydrogen or Me, or Thr($\psi^{z,z}$pro)-OH, wherein Y is Me, and Z is hydrogen or Me.

Pseudoprolines, as α-amino protected dipeptides, are commercially available. For instance, the following pseudoproline dipeptides are used to carry out the present invention:

P-Thr(tBu)-Ser($\Psi^{z,z}$pro)$^8$-OH
P-Val-Ser($\psi^{z,z}$pro)$^{11}$-OH
P-Ser-Ser($\psi^{z,z}$pro)$^{12}$-OH
P-Phe-Thr($\psi^{z,z}$pro)$^7$-OH
P-Gly-Thr($\psi^{z,z}$pro)$^5$-OH wherein P is an α-amino protecting group, and Z is as defined above.

Preferably, the pseudoproline dipeptides used to carry out the present invention are selected from the group consisting of:

Fmoc-Thr(tBu)-Ser($\Psi^{Me,Me}$pro)$^8$-OH
Fmoc-Thr(tBu)-Ser($\Psi^{H,H}$pro)$^8$-OH
Fmoc-Val-Ser($\psi^{Me,Me}$pro)$^{11}$-OH
Fmoc-Val-Ser($\psi^{H,H}$pro)$^{11}$-OH
Fmoc-Ser(tBu)-Ser($\psi^{Me,Me}$pro)$^{12}$-OH
Fmoc-Ser(tBu)-Ser($\psi^{H,H}$pro)$^{12}$-OH
Fmoc-Phe-Thr($\psi^{Me,Me}$pro)$^7$-OH
Fmoc-Phe-Thr($\psi^{H,H}$pro)$^7$-OH
Fmoc-Gly-Thr($\psi^{Me,Me}$pro)$^5$-OH
and
Fmoc-Gly-Thr($\psi^{H,H}$pro)$^5$-OH The introduction of pseudoprolines into a peptide sequence can be performed in the solid-phase under standard coupling conditions. Once the peptide is cleaved from the resin by acydolysis, the pseudoproline is hydrolyzed, providing the two corresponding native amino acids.

The term "resin" or "solid support", describes a functionalized insoluble polymer to which an amino acid or a peptide fragment can be attached and which is suitable for amino acids elongation until the full desired sequence is obtained.

The SPPS can be defined as a process in which a peptide anchored by its C-terminal amino acid to a resin is assembled by the sequential addition of the optionally protected amino acids constituting its sequence. It comprises loading a first α-amino-protected amino acid, or peptide, or pseudoproline dipeptide as defined above, onto a resin and is followed by the repetition of a sequence of steps referred to as a cycle, or as a step of elongation, consisting of the cleavage of the α-amino protecting group and the coupling of the subsequent protected amino acid.

The formation of a peptide bond between two amino acids, or between an amino acid and a peptide fragment, or between two peptide fragments, may involve two steps. First, the activation of the free carboxyl group for a time ranging from 5 minutes to 2 hours, then the nucleophilic attack of the amino group at the activated carboxylic group.

The cycle may be repeated sequentially until the desired sequence of the peptide is accomplished.

Finally, the peptide is deprotected and/or cleaved from the resin.

As a reference for SPPS, please see for instance Knud J. Jensen et al. (eds.), *Peptide Synthesis and Applications*, Methods in Molecular Biology, vol. 1047, Springer Science, 2013.

In a preferred aspect of present invention, an acid sensitive resin is used. More preferably, it is selected from Wang resin, 2-chlorotrityl chloride (CTC) resin, trityl chloride resin, MBH and 4-MeO-BH resin. More preferably, the resin is selected from Wang resin, 2-chlorotrityl chloride (CTC) resin and trityl chloride resin.

Even more preferably, Wang and MBH resin are used for the preparation of fragment B and are therefore involved in the coupling of fragment A with fragment B. Even more preferably, Wang resin is used for the preparation of fragment B and is therefore involved in the coupling of fragment A with fragment B.

Preferably, CTC resin is used for the preparation of fragment A, and fragment A is cleaved from the resin before coupling with fragment B.

In a preferred aspect of present invention, the loading of the first C-terminal amino acid onto the Wang resin is carried out after swelling of the resin in a suitable solvent, preferably DMF, filtering of the resin and adding to the resin the solution of the protected amino acid with an activating agent, such as a carbodiimide, in presence of a base, such as dimethylaminopyridine (DMAP). In case of using a trityl chloride resin, and in particular the CTC resin, after swelling of the resin in a suitable solvent, preferably DCM, and filtering of the resin, a solution of the protected amino acid with an organic base, preferably diisopropylethylamine (DIEA), is added.

In a further preferred aspect of the present invention, for the preparation of fragment A, the first step is the loading of the suitable pseudoproline dipeptide onto the CTC resin, after swelling of the resin in a suitable solvent, preferably DCM.

In a preferred aspect of the present invention, after the first C-terminal amino acid or pseudoproline dipeptide has been loaded onto the resin, an additional step to block unreacted sites is performed to avoid truncated sequences and to prevent any side reactions. Such step is often referred to as "capping".

Capping is achieved by a short treatment of the loaded resin with a large excess of a highly reactive unhindered reagent, which is chosen according to the unreacted sites to be capped.

When using a Wang resin, the unreacted sites are hydroxyl groups, which are preferably capped by treatment with an acid derivative, such as an anhydride, in a basic medium, for instance with a DMF/DIEA/Ac$_2$O mixture, preferably with a 17/2/1 v/v/v or with a 5/2/1 v/v/v composition, or with a Ac$_2$O 10% DMF solution.

When using a CTC resin, the unreacted sites are chlorines, which are preferably capped by treatment with an alcohol in a basic medium, for instance with a DCM/DIEA/MeOH mixture, preferably with a 17/2/1 v/v/v composition. Then, after washing with DCM, the resin is further treated with a DCM/DIEA/Ac$_2$O mixture, preferably with a 17/2/1 v/v/v composition, to cap the hydroxyl groups possibly resulting from the chlorine hydrolysis.

As an alternative to the loading of the first C-terminal amino acid, preloaded resins are used in the preparation of peptide fragments. These are commercially available Wang/CTC resins with attached Fmoc-protected L- or D-amino acids. Accordingly, for instance, Fmoc-Gly-Wang resin is preferably used for the synthesis of fragment B, and Fmoc-pseudoproline-resin can be used for the synthesis of fragment A.

In a preferred aspect of present invention, the loading of the first C-terminal amino acid onto the resin is determined spectrophotometrically, as described for instance in Knud J. Jensen et al. (eds.), *Peptide Synthesis and Applications*, Methods in Molecular Biology, vol. 1047, Springer Science, 2013.

In a preferred aspect of present invention, each amino acid may be protected at its α-amino group and/or at its side-chain functional groups.

Preferably, the protecting group for the amino acids α-amino groups that is used for the SPPS is of the carbamate type. The most preferred protecting groups are the 9-fluorenylmethoxycarbonyl (Fmoc) group, which can be removed under basic conditions, and the tert-butyloxycarbonyl (Boc) group, which can be removed under acid conditions.

The amino acids side-chain functional groups are optionally protected with groups which are generally stable during coupling steps and during α-amino protecting group removal, and which are themselves removable in suitable conditions. Such suitable conditions are generally orthogonal to the conditions in which the α-amino groups are deprotected. The protecting groups of amino acids side-chain functional groups which are used in the present disclosure are generally removable in acidic conditions, as orthogonal to the basic conditions generally used to deprotect Fmoc protecting groups.

In a preferred aspect of present invention, such side-chain protecting groups are specified per individual amino acid occurring in the relevant GLP-1 analogue sequence, as follows:

the arginine (Arg) guanidinium group is preferably protected by a protecting group selected from the group consisting of methoxy-2,3,6-trimethylbenzenesulfonyl (Mtr), 2,2,5,7,8-pentamethylchromanyl-6-sulfonyl (Pmc) and 2,2,4,6,7-pentamethyl-dihydrobenzofuran-5-sulfonyl (Pbf), all removable in acidic conditions; more preferably, the Pbf group is used;

the hydroxyl group of serine (Ser), threonine (Thr), or tyrosine (Tyr) is preferably protected by a group selected from the group consisting of trityl (Trt), tertbutyldimethylsilyl (TBDMS) and tertbutyl (tBu); more preferably, the tBu group is used;

the carboxylic group of glutamic (Glu) or aspartic (Asp) acid is preferably protected by a group selected from the group consisting of 2-phenylisopropyl (2-Phi-Pr), tBu ester, benzyl ester (OBzl), allyl ester (OAll); more preferably, the tBu ester is used;

the indole nitrogen of tryptophan (Trp) is preferably protected by a group selected from the group consisting of tert-butyloxycarbonyl (Boc), formyl (For); more preferably, the tert-butyloxycarbonyl (Boc) group is used;

the imidazole nitrogen of histidine (His) is preferably protected by a group selected from the group consisting of tert-butyloxycarbonyl (Boc), monomethoxytrityl (Mmt), 3-methoxybenzyloxymethyl (MBom), 2-chlorotrityl (Clt), trityl (Trt); more preferably, the trityl (Trt) group is used.

Commercially available protected L-amino acids are generally used. As to the introduction of the lipophilic albumin binding moiety $X_2$ on $Lys^{20}$, in the preparation of liraglutide the commercially available Fmoc-Lys(Pal-Glu-OtBu)-OH depicted herebelow is used:

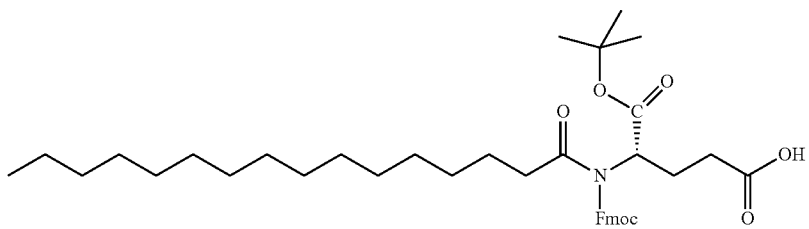

In the preparation of semaglutide, the protected lysine derivative depicted herebelow is used:

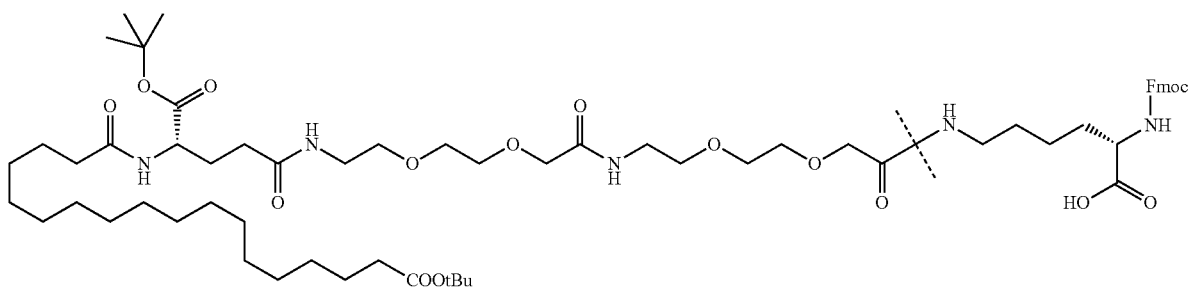

Such derivative is commercially available, and its preparation is also described for instance in CN104356224. Such derivative is also indicated as Fmoc-Lys[(tBuOOC—$(CH_2)_{16}$—CO-γGlu-OtBu)-AEEA-AEEA]-OH, wherein AEEA stands for 2-[2-(2-aminoethoxy)ethoxy]acetyl.

The tBu esters protecting groups of the $X_2$ moiety building blocks are all removable in acidic conditions and are therefore cleaved at the end of the preparation process.

In a preferred aspect of present invention, the coupling steps are performed in the presence of a coupling reagent. Preferably, the coupling reagent is selected from the group consisting of N-hydroxysuccinimide (NHS), N,N'-diisopropylcarbodiimide (DIC), N,N'-dicyclohexylcarbodiimide (DCC), (Benzotriazol-1-yloxy)tripyrrolidinophosphonium hexafluorophosphate (PyBOP), 2-(7-Aza-1H-benzotriazole-1-yl)-1,1,3,3-tetramethyluronium hexafluorophosphate (HATU), 2-(1H-benzotriazole-1-yl)-1,1,3,3-tetramethyluronium hexafluorophosphate (HBTU) and ethyl-dimethylaminopropyl carbodiimide (EDC). More preferably, the reaction is carried out in the presence of N,N'-diisopropylcarbodiimide.

In a preferred aspect of present invention, the coupling steps are performed also in the presence of an additive. The presence of an additive, when used in the coupling reaction, reduces loss of configuration at the carboxylic acid residue, increases coupling rates and reduces the risk of racemization.

Preferably, the additive is selected from the group consisting of 1-hydroxybenzotriazole (HOBt), 2-hydroxypyridine N-oxide, N-hydroxysuccinimide (NHS), 1-hydroxy-7-azabenzotriazole (HOAt), endo-N-hydroxy-5-norbornene-2,3-dicarboxamide, 5-(Hydroxyimino)1,3-dimethylpyrimidine-2,4,6-(1H,3H,5H)-trione (Oxyma-B) and ethyl 2-cyano-2-hydroxyimino-acetate (OxymaPure). More preferably, the additive is selected from the group consisting of 1-hydroxybenzotriazole (HOBt), 2-hydroxypyridine N-oxide, N-hydroxysuccinimide (NHS), 1-hydroxy-7-azabenzotriazole (HOAt), endo-N-hydroxy-5-norbornene-2,3-dicarboxamide, and ethyl 2-cyano-2-hydroxyimino-acetate (OxymaPure). Even more preferably, the reaction is carried out in the presence of 2-cyano-2-hydroxyimino-acetate.

In a preferred aspect, the coupling steps are performed in the presence of a detergent. The preferred detergents for the coupling of fragments according to described synthesis are non-ionic detergents, for instance Triton X-100 (also referred to as TX-100 or as polyethylene glycol tert-octylphenyl ether) or Tween 20, and most preferably Triton X-100. For instance, TX-100 is used as 1% solution in DMF:DCM 50:50 v/v.

In a preferred aspect of present invention, the coupling steps are performed in a solvent selected from the group consisting of DMF, DCM, THF, NMP, DMA or mixtures thereof. More preferably, the coupling is carried out in DMF when a Wang resin is used, and it is carried out in DCM when a CTC resin is used.

In a preferred aspect of present invention, the coupling steps are carried out at a temperature which can vary in the range 10-70° C. Preferably, the temperature varies in the range from room temperature (i.e. 20° C.) to 50° C., more preferably the temperature varies in the range 35-45° C., even more preferably the coupling step is carried out at 40° C.

In a preferred aspect of present invention, the α-amino protecting groups are cleaved in basic conditions. In particular, the Fmoc protecting group is cleaved by treatment with a suitable secondary amine selected from the group consisting of piperidine, pyrrolidine, piperazine and DBU, preferably piperidine. More preferably, Fmoc deprotection is carried out by using a 20% solution of piperidine in DMF.

In another preferred aspect of present invention, the α-amino protecting groups are cleaved in acid conditions. In particular, the Boc protecting group is cleaved by treatment with a strong acidic solution, for instance with trifluoroacetic acid (TFA), hydrochloric acid (HCl) or phosphoric acid ($H_3PO_4$). More preferably, Boc deprotection is carried out during the cleavage of the peptide or peptide fragment from the resin by treatment with a TFA based mixture, which is selected according to the type of resin. For instance, a mixture TFA/water/phenol/TIS (v/v/v/v 88/5/5/2) is used for a Wang resin, wherein TIS is a scavenger, as also described below.

In a preferred aspect of the present invention, once the desired peptide fragment or final peptide has been obtained according to SPPS or CSPPS as described above and is attached to its solid support, the final deprotection and/or cleavage from such solid support is performed. Preferably, such step is performed by using a specific mixture individualised for the resin used, in acidic or slightly acidic conditions.

When a CTC resin is used, the cleavage step is preferably performed by treatment using a mixture of HFIP:DCM (30:70 v/v) or 1-2 v/v % TFA solution in DCM. In particular, when a CTC resin is used in the preparation of fragment A or another fragment, such cleavage does not remove the α-amino protecting group nor the side-chain protecting groups, thus yielding a full protected fragment, ready to react at its free C-terminal carboxylic acid.

When a Wang resin is used, the treatment with a cleavage mixture, comprising TFA and scavengers, provides both side-chains deprotection, including $X_2$ moiety deprotection, and cleavage from the resin. In particular, when a Wang resin is used in the preparation of fragment B, final cleavage yields the crude GLP-1 analogue. Scavengers are substances, like, for instance, anisole, thioanisole, triisopropylsilane (TIS), 1,2-ethanedithiol and phenol, capable of minimize modification or destruction of the sensitive deprotected side chains, such as those of arginine residues, in the cleavage environment. Such cleavage/deprotection step is preferably performed by using a mixture of TFA/thioanisole/anisole/dodecanethiol, for instance with v/v/v/v 90/5/2/3 composition, or a mixture of TFA/water/phenol/TIS, for instance with v/v/v/v 88/5/5/2.

In a preferred aspect of present invention, the crude peptide obtained by cleavage from the resin, be it a fragment or final GLP-1 analogue, is purified to increase its purity.

To this aim, a solution of the peptide is loaded onto an HPLC column with a suitable stationary phase, preferably C18 or C8 modified silica, and an aqueous mobile phase comprising an organic solvent, preferably acetonitrile or methanol, is passed through the column. A gradient of the mobile phase is applied, if necessary. The peptide with desired purity is collected and optionally lyophilized.

Accordingly, the present invention provides a convergent method for the preparation of liraglutide or semaglutide in solid phase synthesis, wherein the method comprises the final coupling of at least one protected N-terminal pseudoproline fragment A with a protected C-terminal fragment B, followed by simultaneous or sequential deprotection and cleavage from the solid support, and optionally final purification by chromatography.

The present invention further provides intermediate fragments A and B and methods for their preparation.

In one aspect, fragment A is an N-terminal fragment of the desired GLP-1 analogue peptide, having a pseudoproline at the C-terminal reactive site. In a preferred aspect, fragment A is protected at its α-amino group, even more preferably with a Boc group. In another preferred aspect, fragment A is protected at its side-chain functional groups with suitable protecting groups.

Fragment A is selected from the group consisting of:

His-$X_1$-Glu-Gly-Thr-Phe-Thr-Ser($\psi^{z,z}$pro) (SEQ ID No 3), also referred to as fragment A (1-8), His-$X_1$-Glu-Gly-Thr-Phe-Thr-Ser-Asp-Val-Ser($\psi^{z,z}$pro) (SEQ ID No 4), also referred to as fragment A (1-11), His-$X_1$-Glu-Gly-Thr-Phe-Thr-Ser-Asp-Val-Ser-Ser($\psi^{z,z}$pro) (SEQ ID No 5), also referred to as fragment A (1-12), His-$X_1$-Glu-Gly-Thr-Phe-Thr($\psi^{z,z}$pro) (SEQ ID No 6), also referred to as fragment A (1-7), and His-$X_1$-Glu-Gly-Thr($\psi^{z,z}$pro) (SEQ ID No 7), also referred to as fragment A (1-5)

wherein $X_1$ is Ala for liraglutide and Aib for semaglutide, and wherein ($\psi^{z,z}$pro) indicates the pseudoproline used, and has the meaning as defined above.

Preferably, fragment A is selected from the group consisting of (SEQ ID No 3)
Boc-His-$X_1$-Glu-Gly-Thr-Phe-Thr-Ser($\psi^{Me,Me}$pro)-OH, (SEQ ID No 4)
Boc-His-$X_1$-Glu-Gly-Thr-Phe-Thr-Ser-Asp-Val-Ser($\psi^{Me,Me}$pro), (SEQ ID No 5)
Boc-His-$X_1$-Glu-Gly-Thr-Phe-Thr-Ser-Asp-Val-Ser-Ser($\psi^{Me,Me}$pro), (SEQ ID No 6)
Boc-His-$X_1$-Glu-Gly-Thr-Phe-Thr($\psi^{Me,Me}$pro)
and (SEQ ID No 7)
Boc-His-$X_1$-Glu-Gly-Thr($\psi^{Me,Me}$pro), wherein $X_1$ and ($\psi^{Me,Me}$pro) are as defined above.

More preferably, for the preparation of liraglutide, fragment A is selected from the group consisting of:

(SEQ ID No 3)
Boc-His(Trt)$^1$-Ala-Glu(OtBu)-Gly-Thr(tBu)-Phe-Thr(tBu)-Ser($\psi^{Me,Me}$pro)$^8$-OH, (SEQ ID No 4)
Boc-His(Trt)$^1$-Ala-Glu(OtBu)-Gly-Thr(tBu)-Phe-Thr(tBu)-Ser(tBu)-Asp(OtBu)-Val-Ser($\psi^{Me,Me}$pro)$^{11}$-OH, (SEQ ID No 5)
Boc-His(Trt)$^1$-Ala-Glu(OtBu)-Gly-Thr(tBu)-Phe-Thr(tBu)-Ser(tBu)-Asp(OtBu)-Val-Ser(tBu)-Ser($\psi^{Me,Me}$pro)$^{12}$-OH, (SEQ ID No 6)
Boc-His(Trt)$^1$-Ala-Glu(OtBu)-Gly-Thr(tBu)-Phe-Thr($\psi^{Me,Me}$pro)$^7$-OH, (SEQ ID No 7)
Boc-His(Trt)$^1$-Ala-Glu(OtBu)-Gly-Thr($\psi^{Me,Me}$pro)$^5$-OH,

```
                                                        (SEQ ID No 3)
Boc-His(Trt)¹-Aib-Glu(OtBu)-Gly-Thr(tBu)-

Phe-Thr(tBu)-Ser(ψ^{Me,Me}pro)⁸-OH, (SEQ ID No 4)
Boc-His(Trt)¹-Aib-Glu(OtBu)-Gly-Thr(tBu)-

Phe-Thr(tBu)-Ser(tBu)-Asp(OtBu)-Val-

Ser(ψ^{Me,Me}pro)¹¹-OH, (SEQ ID No 5)
Boc-His(Trt)¹-Aib-Glu(OtBu)-Gly-Thr(tBu)-

Phe-Thr(tBu)-Ser(tBu)-Asp(OtBu)-Val-Ser(tBu)-

Ser(ψ^{Me,Me}pro)¹²-OH, (SEQ ID No 6)
Boc-His(Trt)¹-Aib-Glu(OtBu)-Gly-Thr(tBu)-

Phe-Thr(ψ^{Me,Me}pro)⁷-OH
and (SEQ ID No 7)
Boc-His(Trt)¹-Aib-Glu(OtBu)-Gly-

Thr(ψ^{Me,Me}pro)⁵-OH.
```

Even more preferably, fragment A is

Boc-His(Trt)¹-Ala-Glu(OtBu)-Gly-Thr(tBu)-Phe-Thr(tBu)-Ser(Ψ^{Me,Me}pro)⁸-OH (SEQ ID No 3), also referred to as fragment 4, which is a specified form of fragment A (1-8).

In another embodiment, wherein the preparation of semaglutide is pursued, fragment A is preferably Boc-His-Aib-Glu-Gly-Thr-Phe-Thr-Ser(ψ^{Me,Me}pro) (SEQ ID No 3)

and even more preferably

Boc-His(Trt)¹-A(b-Glu(OtBu)-Gly-Thr(tBu)-Phe-Thr(tBu)-Ser(Ψ^{Me,Me}pro)⁸-OH (SEQ ID No 3), also referred to as fragment 7, which is a specified form of fragment A (1-8).

Fragment A is prepared either by stepwise SPPS or by LPPS. For instance, fragment A is prepared in solid phase by starting with the loading onto a resin of the suitable C-terminal pseudoproline dipeptide, for instance Fmoc-Thr(tBu)-Ser(Ψ^{Me,Me}pro)⁸-OH, and subsequently elongating the peptide chain by coupling the sequence amino acids one-by-one, by alternating coupling and α-amino group deprotection steps.

Preferably, stepwise Fmoc SPPS on a CTC resin is used in the preparation of fragment A, and the synthesis is completed by using a Boc-protected last amino acid, i.e. Boc-His(Trt)-OH. Once its sequence has been completed, fragment A is cleaved from the solid support while retaining both α-amino group and side-chain protecting groups.

As examples for the preparation of fragment A, the preparation of fragment 4 and of fragment 7 are described in the Examples of present disclosure.

Analogously, all fragments A defined above are prepared in a similar way.

In another embodiment, fragment B is a C-terminal fragment of the desired GLP-1 analogue peptide, bound to a solid support, which is preferably a Wang resin. In another preferred embodiments the solid support is a MBH resin.

Fragment B is selected from the group consisting of

```
                                                        (SEQ ID No 8)
Asp-Val-Ser-Ser-Tyr-Leu-Glu-Gly-Gln-

Ala-Ala-Lys(X₂)-Glu-Phe-Ile-Ala-Trp-Leu-

Val-Arg-Gly-Arg-Gly-Wang resin, (SEQ ID No 9)
Ser-Tyr-Leu-Glu-Gly-Gln-Ala-Ala-Lys(X₂)-

Glu-Phe-Ile-Ala-Trp-Leu-Val-Arg-Gly-

Arg-Gly-Wang resin, (SEQ ID No 10)
Tyr-Leu-Glu-Gly-Gln-Ala-Ala-Lys(X₂)-

Glu-Phe-Ile-Ala-Trp-Leu-Val-Arg-Gly-

Arg-Gly-Wang resin, (SEQ ID No 11)
Ser-Asp-Val-Ser-Ser-Tyr-Leu-Glu-Gly-Gln-

Ala-Ala-Lys(X₂)-Glu-Phe-Ile-Ala-Trp-Leu-

-Val-Arg-Gly-Arg-Gly-Wang resin,
and (SEQ ID No 12)
Phe-Thr-Ser-Asp-Val-Ser-Ser-Tyr-Leu-Glu- Gly-Gln-Ala-Ala-Lys(X₂)-Glu-Phe-Ile-Ala- Trp-Leu-Val-Arg-Gly-Arg-Gly-Wang resin,
``` wherein

X₂ is N-(1-oxohexadecyl)-L-γ-glutamyl (Pal-Glu) for the synthesis of liraglutide, and X₂ is N-(17-carboxy-1-oxoheptadecyl)-L-γ-glutamyl-2-[2-(2-aminoethoxy)ethoxy]acetyl-2-[2-(2-aminoethoxy)ethoxy]acetyl for the synthesis of semaglutide.

Preferably, for the preparation of liraglutide, fragment B is selected from the group consisting of

```
H-Asp(OtBu)⁹-Val-Ser(tBu)-Ser(tBu)-Tyr(tBu)-

Leu-Glu(OtBu)-Gly¹⁶-Gln(Trt)-Ala-Ala-Lys(Pal-

Glu-OtBu)-Glu(OtBu)-Phe-Ile-Ala-Trp(NmBoc)-

Leu-Val-Arg(Pbf)-Gly-Arg(Pbf)-Gly³¹-Wang
resin (SEQ ID No 8),
also referred to as fragment 3, (SEQ ID No 9)
H-Ser(tBu)-Tyr(tBu)-Leu-Glu(OtBu)-Gly¹⁶-

Gln(Trt)-Ala-Ala-Lys(Pal-Glu-OtBu)-Glu(OtBu)-

Phe-Ile-Ala-Trp(N^{in}Boc)-Leu-Val-Arg(Pbf)-

Gly-Arg(Pbf)-Gly³¹-Wang resin, (SEQ ID No 10)
H-Tyr(tBu)-Leu-Glu(OtBu)-Gly¹⁶-Gln(Trt)-Ala- Ala-Lys(Pal-Glu-OtBu)-Glu(OtBu)-Phe-Ile-Ala- Trp(N^{in}Boc)-Leu-Val-Arg(Pbf)-Gly-Arg(Pbf)-

Gly³¹-Wang resin,
```

```
                                                   (SEQ ID No 11)
H-Ser(tBu)-Asp(OtBu)9-Val-Ser(tBu)-Ser(tBu)-

Tyr(tBu)-Leu-Glu(OtBu)-Gly16-Gln(Trt)-Ala-Ala-

Lys(Pal-Glu-OtBu)-Glu(OtBu)-Phe-Ile-Ala-

Trp(NmBoc)-Leu-Val-Arg(Pbf)-Gly-Arg(Pbf)-

Gly31-Wang resin
and (SEQ ID No 12)
H-Phe-Thr(tBu)-Ser(tBu)-Asp(OtBu)9-Val-

Ser(tBu)-Ser(tBu)-Tyr(tBu)-Leu-Glu(OtBu)-

Gly16- Gln(Trt)-Ala-Ala-Lys(Pal-Glu-OtBu)-

Glu(OtBu)-Phe-Ile-Ala-Trp(NmBoc)-Leu-Val-

Arg(Pbf)-Gly-Arg(Pbf)-Gly31-

Wang resin.
```

Even more preferably, for the preparation of liraglutide, fragment B is:

H-Asp(OtBu)$^9$-Val-Ser(tBu)-Ser(tBu)-Tyr(tBu)-Leu-Glu (OtBu)-Gly$^{16}$-Gln(Trt)-Ala-Ala-Lys(Pal-Glu-OtBu)-Glu (OtBu)-Phe-Ile-Ala-Trp(N$^{in}$Boc)-Leu-Val-Arg(Pbf)-Gly-Arg(Pbf)-Gly$^{31}$-Wang resin (SEQ ID No 8), also referred to as fragment 3, which is a specified form of fragment B (9-31).

In another embodiment wherein the preparation of semaglutide is pursued, fragment B is preferably

```
                                                    (SEQ ID No 8)
Asp-Val-Ser-Ser-Tyr-Leu-Glu-Gly-Gln-Ala-

Ala-Lys[(ROOC-(CH2)16—CO-yGlu-OR')-AEEA-

AEEA]Glu-Phe-Ile-Ala-Trp-Leu-Val-Arg-Gly-

Arg-Gly-resin,
``` wherein R and R', same or different, are carboxylic acid protective groups, preferably esters; more preferably fragment B is H-Asp(OtBu)$^9$-Val-Ser(tBu)-Ser(tBu)-Tyr(tBu)-Leu-Glu(OtBu)-Gly-Gln(Trt)-Ala-Ala-Lys[(tBuOOC—(CH$_2$)$_{16}$—CO-γGlu-OtBu)-AEEA-AEEA]-Glu-(OtBu)-Phe-Ile-Ala-Trp(N$^{in}$Boc)-Leu-Val-Arg(Pbf)-Gly-Arg(Pbf)-Gly$^{31}$-MBH resin (SEQ ID No 8), also referred to as fragment 6, which is a specified form of fragment B (9-31).

Fragment B is prepared either by stepwise SPPS, or by CSPPS, or by LPPS. For instance, fragment B is prepared in solid phase by starting with the loading on the resin of the protected C-terminal amino acid, i.e. Gly$^{31}$, and subsequently elongating the peptide chain by coupling the sequence amino acids one-by-one, by alternating coupling and α-amino group deprotection steps. Alternatively, fragment B is prepared by CSPPS by coupling two or more peptide fragments.

In a preferred embodiment of the present invention, the preparation of fragment B comprises coupling the suitable N-terminal fragment C to C-terminal fragment D, according to Scheme 2:

fragment C-COOH + NH$_2$-fragment D-solid support

NH$_2$-fragment B-solid support

Fragment D is attached to a solid support through Gly$^{31}$ and is preferably protected at its amino acids side chains. In a preferred embodiment of the present invention, fragment D is

```
Gln17-Ala-Ala-Lys(X2)-Glu-Phe-Ile-Ala-

Trp-Leu-Val-Arg-Gly-Arg-Gly31-resin
(SEQ ID No 13), also referred
to as fragment D (17-31).
```

Fragment C is a suitable fragment selected from the group consisting of:

```
Asp-Val-Ser-Ser-Tyr-Leu-Glu-Gly
(SEQ ID No 14), also referred
to as fragment C (9-16), Ser-Tyr-Leu-Glu-Gly
(SEQ ID No 15), also referred
to as fragment C (12-16), Tyr-Leu-Glu-Gly
(SEQ ID No 16), also referred
to as fragment C (13-16)

Ser-Asp-Val-Ser-Ser-Tyr-Leu-Glu-Gly
(SEQ ID No 17), also referred
to as fragment C (8-16)
and Phe-Thr-Ser-Asp-Val-Ser-Ser-Tyr- Leu-Glu-Gly
(SEQ ID No 18),
referred to as fragment C (6-16).
```

Fragment C has a C-terminal glycine which is conveniently reacted to form the required amide bond in the conditions discussed above. Fragment C is also preferably protected at its amino acids side chains and at its α-amino group.

Fragment C is preferably selected from the group consisting of:

```
                                                    (SEQ ID No 14)
Fmoc-Asp(OtBu)9-Val-Ser(tBu)-Ser(tBu)-

Tyr(tBu)-Leu-Glu(OtBu)-Gly16-OH, (SEQ ID No 15)
Fmoc-Ser(tBu)-Tyr(tBu)-Leu-Glu(OtBu)-

Gly16-OH, (SEQ ID No 16)
Fmoc-Tyr(tBu)-Leu-Glu(OtBu)-Gly16-OH, (SEQ ID No 17)
Fmoc-Ser(tBu)-Asp(OtBu)9-Val-Ser(tBu)-

Ser(tBu)-Tyr(tBu)-Leu-Glu(OtBu)-Gly16-OH
and
```

-continued

```
                                             (SEQ ID No 18)
Fmoc-Phe-Thr(tBu)-Ser(tBu)-Asp(OtBu)⁹-

Val-Ser(tBu)-Ser(tBu)-Tyr(tBu)-Leu-

Glu(OtBu)-Gly¹⁶-OH.
```

Most preferably, fragment C is Fmoc-Asp(OtBu)⁹-Val-Ser(tBu)-Ser(tBu)-Tyr(tBu)-Leu-Glu(OtBu)-Gly¹⁶-OH (SEQ ID No 14), also referred to as fragment 2.

Such fragment C is conveniently used for the preparation of both liraglutide and semaglutide, as it will be described in the Examples of the present disclosure.

In a more preferred embodiment of the present invention

```
                                             (SEQ ID No 20)
Asp-Val-Ser-Ser-Tyr-Leu-Glu-Gly-Gln-Ala-Ala-

Lys(X₂)-Glu-Phe-Ile-Ala-Trp-Leu-Val-Arg-Gly-

Arg-Gly-Wang resin
``` is obtained by a fragment C (9-16)+fragment D (17-31) coupling strategy, preferably by coupling

```
                                             (SEQ ID No 14)
Asp9-Val-Ser-Ser-Tyr-Leu-Glu-Gly¹⁶-OH
``` with

```
                                             (SEQ ID No 13)
H-Gln-Ala-Ala-Lys(X₂)-Glu-Phe-Ile-Ala-Trp-

Leu-Val-Arg-Gly-Arg-Gly³¹ resin
``` wherein $X_2$ is N-(1-oxohexadecyl)-L-γ-glutamyl for the synthesis of liraglutide, and $X_2$ is N-(17-carboxy-1-oxoheptadecyl)-L-γ-glutamyl-2-[2-(2-aminoethoxy)ethoxy]acetyl-2-[2-(2-aminoethoxy)ethoxy]acetyl for the synthesis of semaglutide;

and wherein the resin preferably is a Wang resin.

In an even more preferred embodiment, whenever liraglutide preparation is pursued, preferred fragment 3 (i.e. H-Asp(OtBu)⁹-Val-Ser(tBu)-Ser(tBu)-Tyr(tBu)-Leu-Glu(OtBu)-Gly¹⁶-Gln(Trt)-Ala-Ala-Lys(Pal-Glu-OtBu)-Glu(OtBu)-Phe-Ile-Ala-Trp(N$^{in}$Boc)-Leu-Val-Arg(Pbf)-Gly-Arg(Pbf)-Gly³¹-Wang resin (SEQ ID No 20)) is obtained by a fragment C (9-16)+fragment D (17-31) coupling strategy, preferably by coupling Fmoc-Asp(OtBu)⁹-Val-Ser(tBu)-Ser(tBu)-Tyr(tBu)-Leu-Glu(OtBu)-Gly¹⁶-OH (SEQ ID No 14) (fragment 2)
with H-Gln(Trt)¹⁷-Ala-Ala-Lys(Pal-Glu-OtBu)-Glu-(OtBu)-Phe-Ile-Ala-Trp(N$^{in}$Boc)-Leu-Val-Arg(Pbf)-Gly-Arg(Pbf)-Gly³¹-Wang resin (SEQ ID No 13), fragment 1, a specified fragment D (17-31).

The α-amino protected fragment B (9-31) thus obtained is then treated to cleave the Fmoc group in basic conditions as described above to provide fragment 3 as defined above.

In another preferred embodiment, whenever semaglutide preparation is pursued, preferred fragment 6 (i.e. H-Asp(OtBu)⁹-Val-Ser(tBu)-Ser(tBu)-Tyr(tBu)-Leu-Glu(OtBu)-Gly-Gln(Trt)-Ala-Ala-Lys[(tBuOOC—(CH₂)₁₆—CO-γGlu-OtBu)-AEEA-AEEA]-Glu-(OtBu)-Phe-Ile-Ala-Trp(N$^{in}$Boc)-Leu-Val-Arg(Pbf)-Gly-Arg(Pbf)-Gly³¹-MBH Resin (SEQ ID No 20)) is obtained by a fragment C (9-16)+fragment D (17-31) coupling strategy, preferably by coupling Fmoc-Asp(OtBu)⁹-Val-Ser(tBu)-Ser(tBu)-Tyr(tBu)-Leu-Glu(OtBu)-Gly¹⁶-OH (SEQ ID No 14) (fragment 2)

with
H-Gln(Trt)¹⁷-Ala-Ala-Lys[(tBuOOC—(CH₂)₁₆—CO-γGlu-OtBu)-AEEA-AEEA]-Glu(OtBu)-Phe-Ile-Ala-Trp(N$^{in}$Boc)-Leu-Val-Arg(Pbf)-Gly-Arg(Pbf)-Gly³¹-O-MBH Resin (SEQ ID No 13), fragment 5, a specified fragment D (17-31).

The α-amino protected fragment B (9-31) thus obtained is then treated to cleave the Fmoc group in basic conditions as described above to provide fragment 6 as defined above.

As an example for the preparation of fragment B, the preparation of fragment 3 and of fragment 6 are described in the Examples of the present disclosure, including the preparation of fragment 1, fragment 5 and fragment 2.

Analogously, all fragments B defined above are prepared by the coupling of a suitable fragment C and a suitable fragment D as defined above.

The most preferred embodiment of the method to prepare liraglutide is a method according to the invention wherein:

Fragment A is His-Ala-Glu-Gly-Thr-Phe-Thr-Ser (ψ$^{z,z}$pro) (SEQ ID No 3), also referred to as fragment A (1-8), more preferably Boc-His(Trt)¹-Ala-Glu(OtBu)-Gly-Thr(tBu)-Phe-Thr(tBu)-Ser(ψ$^{Me,Me}$pro)⁸-OH (SEQ ID No 3), also referred to as fragment 4; and Fragment B is Asp-Val-Ser-Ser-Tyr-Leu-Glu-Gly-Gln-Ala-Ala-Lys(Pal-Glu)-Glu-Phe-Ile-Ala-Trp-Leu-Val-Arg-Gly-Arg-Gly-resin (SEQ ID No 8), also referred to as fragment B (9-31), more preferably H-Asp(OtBu)⁹-Val-Ser(tBu)-Ser(tBu)-Tyr(tBu)-Leu-Glu(OtBu)-Gly¹⁶-Gln(Trt)-Ala-Ala-Lys(Pal-Glu-OtBu)-Glu(OtBu)-Phe-Ile-Ala-Trp(N$^{in}$Boc)-Leu-Val-Arg(Pbf)-Gly-Arg(Pbf)-Gly³¹-Wang resin (SEQ ID No 8), also referred to as fragment 3.

It is most preferred in this setting that Fragment C is Asp-Val-Ser-Ser-Tyr-Leu-Glu-Gly (SEQ ID No 14), referred to as fragment C (9-16), more preferably Fmoc-Asp(OtBu)⁹-Val-Ser(tBu)-Ser(tBu)-Tyr(tBu)-Leu-Glu(OtBu)-Gly¹⁶-OH (SEQ ID No 14), also referred to as fragment 2; and Fragment D is Gln¹⁷-Ala-Ala-Lys(Pal-Glu)-Glu-Phe-Ile-Ala-Trp-Leu-Val-Arg-Gly-Arg-Gly³¹-resin (SEQ ID No 13), also referred to as fragment D (17-31), more preferably H-Gln(Trt)¹⁷-Ala-Ala-Lys(Pal-Glu-OtBu)-Glu-(OtBu)-Phe-Ile-Ala-Trp(N$^{in}$Boc)-Leu-Val-Arg(Pbf)-Gly-Arg(Pbf)-Gly³¹-Wang resin (SEQ ID No 13), also referred to as fragment 1.

The most preferred embodiment of the method to prepare semaglutide is a method according to the invention wherein, Fragment A is His-Aib-Glu-Gly-Thr-Phe-Thr-Ser (ψ$^{z,z}$pro) (SEQ ID No 3), also referred to as fragment A (1-8), more preferably Boc-His(Trt)¹-Aib-Glu(OtBu)-Gly-Thr(tBu)-Phe-Thr(tBu)-Ser(ψ$^{Me,Me}$pro)⁸-OH (SEQ ID No 3), also referred to as fragment 7; and Fragment B is Asp-Val-Ser-Ser-Tyr-Leu-Glu-Gly-Gln-Ala-Ala-Lys[(ROOC—(CH₂)₁₆—CO-γGlu-OR')-AEEA-AEEA]-Glu-Phe-Ile-Ala-Trp-Leu-Val-Arg-Gly-Arg-Gly-resin (SEQ iD No 8), also referred to as fragment B (9-31), more preferably H-Asp(OtBu)⁹-Val-Ser(tBu)-Ser(tBu)-Tyr(tBu)-Leu-Glu(OtBu)-Gly-Gln(Trt)-Ala-Ala-Lys[(tBuOOC—(CH₂)₁₆—CO-γGlu-OtBu)-AEEA-AEEA]-Glu-(OtBu)-Phe-Ile-Ala-Trp(N$^{in}$Boc)-Leu-Val-Arg(Pbf)-Gly-Arg(Pbf)-Gly³¹-MBH resin (SEQ ID No 8), also referred to as fragment 6.

It is most preferred in this setting that Fragment C is Asp-Val-Ser-Ser-Tyr-Leu-Glu-Gly, (SEQ ID No 14) also referred to as fragment C (9-16), more preferably Fmoc-Asp(OtBu)⁹-Val-Ser(tBu)-Ser(tBu)-Tyr(tBu)-Leu-Glu(OtBu)-Gly¹⁶-OH (SEQ ID No 14), also referred to as fragment 2; and Fragment D is Gln¹⁷-Ala-Ala-Lys[(ROOC—(CH₂)₁₆—CO-γGlu-OR')-AEEA-AEEA]-Glu-Phe-Ile-Ala-Trp-Leu- Val-Arg-Gly-Arg-Gly$^{31}$-resin (SEQ ID No. 13), also referred to as fragment D (17-31), wherein R and R', same or different, are carboxylic acid protective groups, preferably esters, more preferably H-Gln(Trt)$^{17}$-Ala-Ala-Lys[(tBuOOC—(CH$_2$)$_{16}$—CO-γGlu-OtBu)-AEEA-AEEA]-Glu(OtBu)-Phe-Ile-Ala-Trp(N$^{in}$-Boc)-Leu-Val-Arg(Pbf)-Gly-Arg(Pbf)-Gly$^{31}$-O-MBH resin (SEQ ID No 13), fragment 5.

The convergent fragment-based method for the preparation of GLP-1 analogues described above provides the desired resin bound final peptide, which is treated for simultaneous or sequential deprotection and/or cleavage step to obtain the crude peptide, which is optionally further purified.

Abbreviations

SPPS Solid Phase Peptide Synthesis
LPPS Liquid Phase Peptide Synthesis
CSPPS Convergent Solid Phase Peptide Synthesis
CTC 2-chloro-trityl chloride
MBH 4-Methylbenzhydryl
4-MeO-BH 4-Methoxybenzhydryl
AEEA 2-[2-(2-aminoethoxy)ethoxy]acetyl
Fmoc 9-Fluorenylmethoxycarbonyl
Boc Tert-butyloxycarbonyl
Trt Trityl (triphenylmethyl)
tBu Tert-butyl
Pbf 2,2,4,6,7-Pentamethyl-dihydrobenzofuran-5-sulfonyl
eq. Equivalent
h hour/s
min minute/s
HPLC High Performance Liquid Chromatography
DIEA/DIPEA N,N-Diisopropylethylamine
DBU 1,8-Diazabicyclo[5.4.0]undec-7-ene
DMAP 4-Dimethylaminopyridine
TFA Trifluoroacetic acid
TIS Triisopropylsilane
Ac$_2$O Acetic anhydride
DMF N,N-Dimethylformamide
DMA N,N-Dimethylacetamide
DCM Dichloromethane
THF Tetrahydrofuran
NMP N-Methyl-2-pyrrolidinone
MTBE Methyl-tert-butylether
DIPE diisopropylether
MeOH Methanol
HFIP Hexafluoro-2-propanol
TBDMS Tert-butyl-dimethyl-silyl
DIC N,N'-Diisopropylcarbodiimide
DCC N,N'-Dicyclohexylcarbodiimide
EDC N-(3-dimethylaminopropyl)-N'-ethylcarbodiimide
HOBt 1-Hydroxybenzotriazole
HOAt 1-Hydroxy-7-azabenzotriazole
NHS N-Hydroxysuccinimide
TBTU O-(Benzotriazol-1-yl)-N,N,N',N'-tetramethyluronium tetrafluoroborate
HBTU O-(Benzotriazol-1-yl)-N,N,N',N'-tetramethyluronium hexafluorophosphate
HATU 2-(7-Aza-1H-benzotriazole-1-yl)-1,1,3,3-tetramethyluronium hexafluorophosphate
PyBOP (Benzotriazol-1-yloxy)tripyrrolidinophosphonium hexafluorophosphate
OxymaPure Ethyl 2-cyano-2-hydroxyimino-acetate
Oxyma-B 5-(Hydroxyimino)1,3-dimethylpyrimidine-2,4,6-(1H,3H,5H)-trione
TX-100 Triton X-100, also referred to as polyethylene glycol tert-octylphenyl ether

EXAMPLES

Detailed experimental parameters suitable for the preparation of liraglutide and semaglutide according to the present invention are provided by the following examples, which are intended to be illustrative and not limiting of all possible embodiments of the invention.

Example 1

Preparation of Liraglutide
Step 1. Preparation of Fragment 1, a Fragment D (17-31), (SEQ ID NO 13)

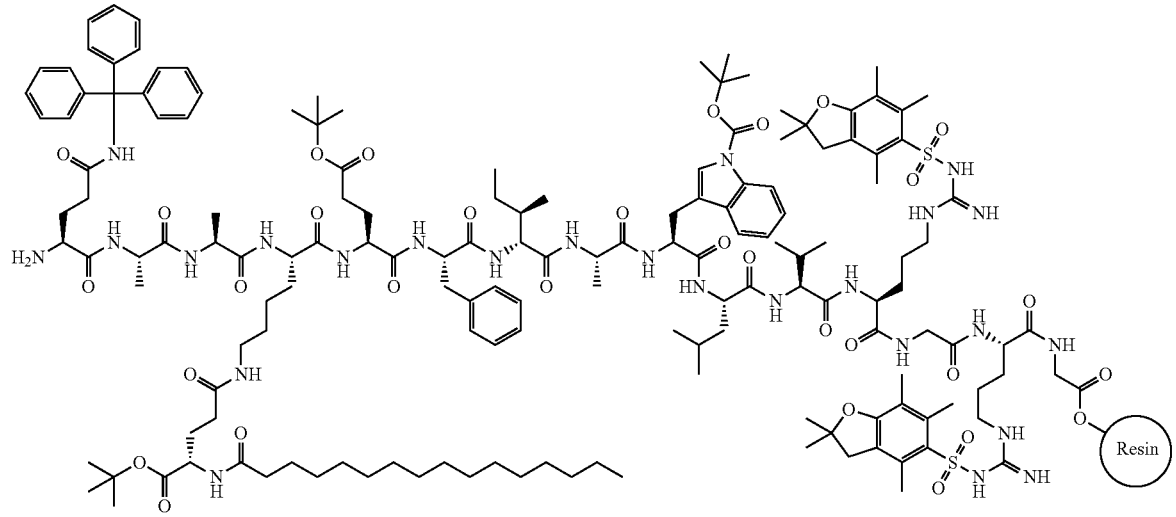

H-Gln(Trt)$^{17}$-Ala-Ala-Lys(Pal-Glu-OtBu)-Glu(OtBu)-Phe-Ile-Ala-Trp(N$^{in}$Boc)-Leu-Val-Arg(Pbf)-Gly-Arg(Pbf)-Gly$^{31}$-Wang resin The synthesis of the peptide fragment 1 was carried out at room temperature by stepwise Fmoc SPPS using 0.25 g of Wang resin (0.75 mmol/g). After swelling of the resin in 2 ml of DMF, Fmoc-Gly-OH, DIC and DMAP (4, 2 and 0.1 eq respectively, referred to the loading of the resin) in DMF were added. After 1 h the unreacted hydroxyl groups of the resin were capped by treatment with DMF/DIPEA/Ac$_2$O mixture (v/v/v 5/2/1) for 30 minutes. Fmoc deprotection was performed with 20% solution of piperidine in DMF (2×2 ml, 5 min and 15 min) and the resin was washed with DMF (4×2 ml). The substitution degree was checked by UV adsorption measurement of the solution collected after Fmoc deprotection and was found to be 0.53 mmol/g. Fmoc-protected amino acids (four-fold excess respect to the loading of the resin) were pre-activated with the mixture of DIC (4 eq) and ethyl 2-cyano-2-(hydroxyimino)acetate (OxymaPure, 4 eq) and consecutively coupled to the resin in 60 min. The completion of the coupling was monitored by ninhydrine test. In case of incomplete reaction the coupling was repeated. For the introduction of Fmoc-Lys(Pal-Glu-OtBu)-OH into the peptide sequence double coupling was carried out using 3 eq and 1.5 eq of palmitoylated dipeptide (9 h and 5 h, respectively). At the end of each coupling the unreacted peptide chains were acylated with acetic anhydride (10 eq) in the presence of DIPEA (10 eq). The intermediate Fmoc deprotections were carried out using 20% solution of piperidine in DMF (2×2 ml, 5 min and 15 min) with following washing of the resin with DMF (4×2 ml). After the completion of the synthesis the resin was washed with DCM and dried.

Step 2. Preparation of Fragment 2, a Fragment C (9-16),

The synthesis of the peptide fragment was carried out by stepwise SPPS using 2-chlorotrityl chloride resin (CTC resin) (0.25 g, 1.6 mmol/g). After swelling of the resin using 3 ml of DCM, Fmoc-Gly-OH and DIEA (0.8 and 3 eq, respect to the loading of the resin) in DCM were added. The reaction mixture was stirred for 1 hour and the solvent was filtered off. The unreacted sites of the resin were capped using a DCM/DIPEA/MeOH mixture (v/v/v 17/2/1) for 30 minutes. After washing with DCM (3×5 ml) the resin was treated with DCM/DIPEA/Ac$_2$O mixture (v/v 5/2/1) for 30 minutes. The loading of the resin was checked by UV adsorption measurement of the solution after Fmoc deprotection and was found to be 1.08 mmol/g. Then Fmoc-Glu(OtBu)-OH, Fmoc-Leu-OH, Fmoc-Tyr(tBu)-OH, Fmoc-Ser(tBu)-OH, Fmoc-Ser(tBu)-OH, Fmoc-Val-OH and Fmoc-Asp(OtBu)-OH (three-fold excess respect to the loading of the resin) were pre-activated by DIC (three-fold excess) and OxymaPure (three-fold excess) and coupled consecutively to the resin in 60 min. The intermediate Fmoc deprotections were carried out using 20% solution of piperidine in DMF (2×2 ml, 5 min and 15 min) with following washing of the resin with DMF (4×2 ml). After the completion of the synthesis the resin was washed with DCM. The protected peptide was cleaved from the resin by the treatment with 1 ml of 1% TFA in DCM for 2 min and the solution was filtered into 2 ml of 10% solution of pyridine in methanol. The procedure was repeated 4 times. Then the resin was washed with DCM (3×2 ml), methanol (3×2 ml) and the combined solutions were concentrated to 5% of the volume. The protected octapeptide was precipitated by addition of water under ice-cold bath, filtered, washed several times by water and dried. Yield: 330 mg (90%), HPLC purity 91%

(SEQ ID NO 14)

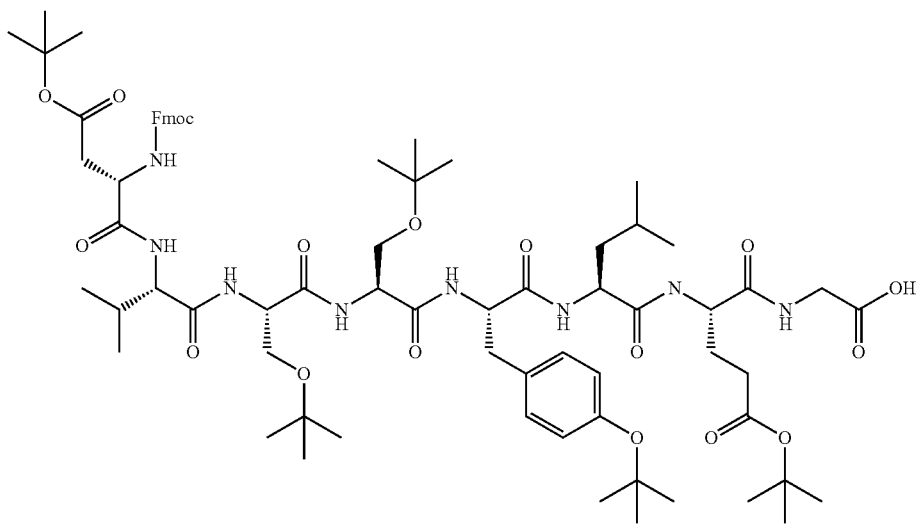

Fmoc-Asp(OtBu)$^9$-Val-Ser(tBu)-Ser(tBu)-Tyr(tBu)-Leu-Glu(OtBu)-Gly$^{16}$-OH

Step 3-a. Condensation of Fragments 1 and 2: Preparation of Fragment 3, a Fragment B (9-31), (SEQ ID No 8)

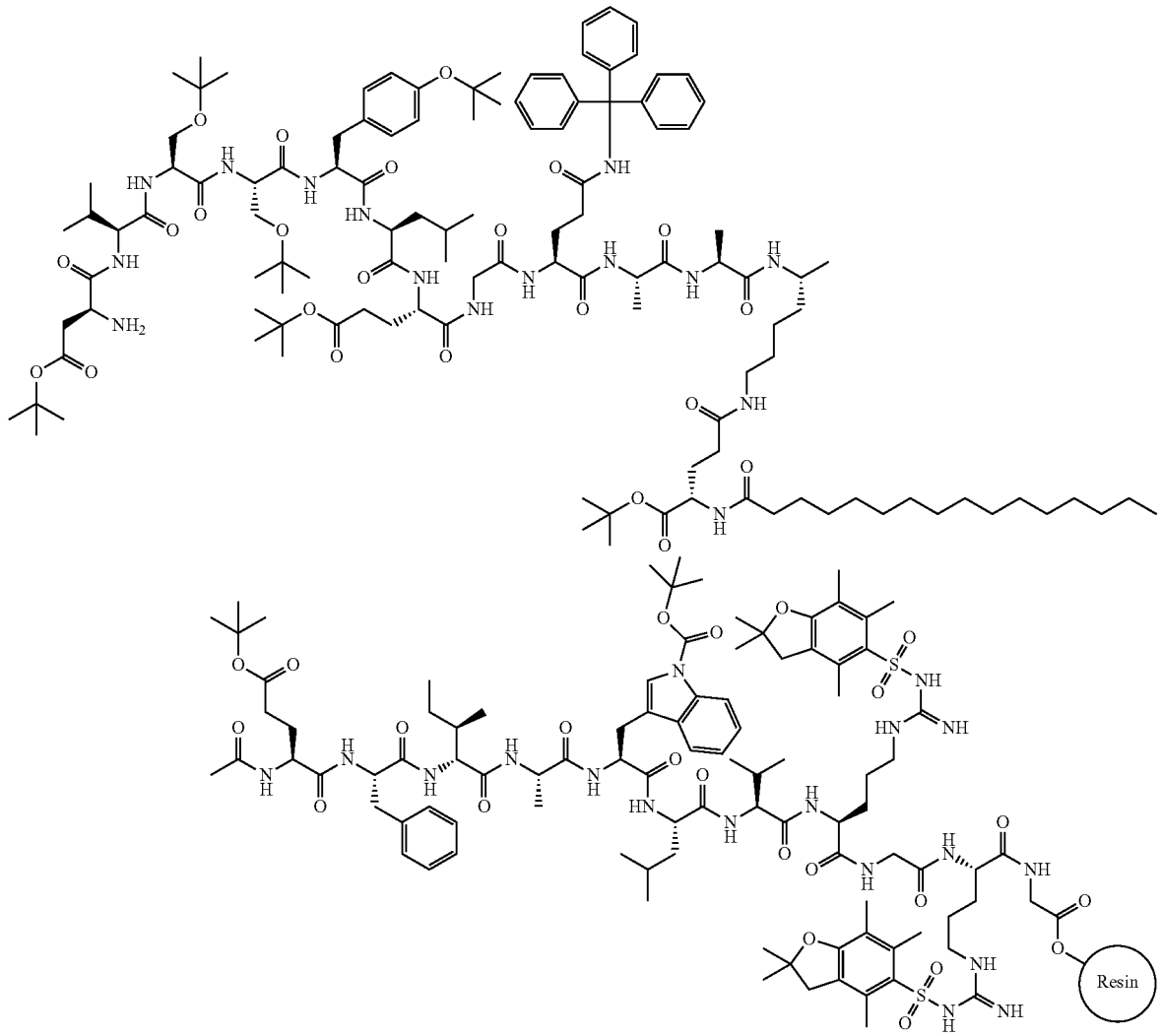

H-Asp(OtBu)$^9$-Val-Ser(tBu)-Ser(tBu)-Tyr(tBu)-Leu-Glu(OtBu)-Gly-Gln(Trt)-Ala-Ala-Lys(Pal-Glu-OtBu)-Glu(OtBu)-Phe-Ile-Ala-Trp(N$^{in}$Boc)-Leu-Val-Arg(Pbf)-Gly-Arg(Pbf)-Gly$^{31}$-Wang resin Peptide fragment 1 obtained in Step 1 was swelled in 2 ml of DMF. Protected fragment 2 (180 mg, 0.13 mmol, 1 eq) was dissolved in 7 ml of DMF, pre-activated with DIC (16 mg, 0.13 mmol), OxymaPure (40 mg, 0.27 mmol) and coupled to fragment 1. The reaction was stirred at 40° C. and monitored with HPLC. Another 1 eq of pre-activated peptide fragment 2 (180 mg, 0.13 mmol) was added at 40° C. and stirred to complete the condensation. The resin was then washed with DMF (2×2 ml) and residual unreacted amino function was capped with 10% solution of Ac$_2$O in DMF (2 ml, 30 min).

Lastly, the Fmoc protective group was removed with 20% solution of piperidine in DMF (2×2 ml, 5 min and 15 min) with following washing of the resin with DMF (3×2 ml).

Step 3-b. Condensation of Fragments 1 and 2 in the Presence of a Detergent: Preparation of Fragment 3, a Fragment B (9-31), H-Asp(OtBu)$^9$-Val-Ser(tBu)-Ser(tBu)-Tyr(tBu)-Leu-Glu(OtBu)-Gly-Gln(Trt)-Ala-Ala-Lys(Pal-Glu-OtBu)-Glu(OtBu)-Phe-Ile-Ala-Trp(N$^{in}$Boc)-Leu-Val-Arg(Pbf)-Gly-Arg(Pbf)-Gly$^{31}$-Wang resin (SEQ ID No 8)

Peptide fragment 1 obtained in Step 1 was swelled in 2 ml of a mixture DMF:DCM 50:50 v/v+1% Triton X-100 (TX-100). Protected fragment 2 (267 mg, 0.195 mmol, 1.5 eq) was dissolved in 5.3 ml of DMF:DCM 50:50 v/v+1% TX-100, pre-activated with DIC (24.6 mg, 0.195 mmol), OxymaPure (27.7 mg, 0.195 mmol) and coupled to fragment 1. The reaction was stirred at 40° C. and monitored by HPLC. The resin was then washed with 2 ml of DMF:DCM 50:50 v/v+1% TX-100 and with DMF (2×2 ml). Residual unreacted amino function was capped with 10% solution of Ac$_2$O in DMF (2 ml, 30 min).

Lastly, the Fmoc protective group was removed with 20% solution of piperidine in DMF (2×2 ml, 5 min and 15 min) with following washing of the resin with DMF (3×2 ml).

Step 4. Preparation of Fragment 4, a Fragment A (1-8), (SEQ ID No 3)

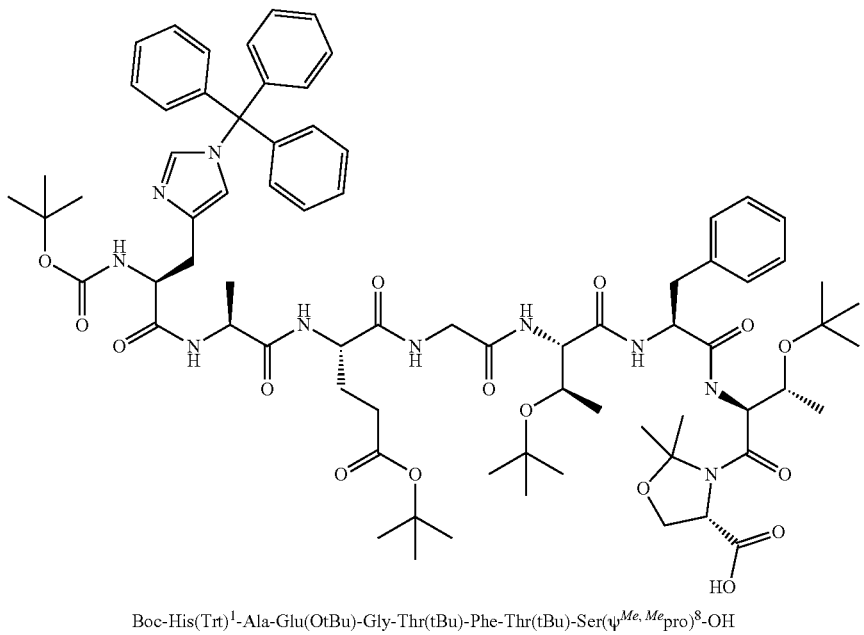

Boc-His(Trt)¹-Ala-Glu(OtBu)-Gly-Thr(tBu)-Phe-Thr(tBu)-Ser(ψ$^{Me, Me}$pro)⁸-OH

Peptide fragment 4 was prepared in a similar way as described in Step 2. At first, the attachment of Fmoc-Thr(tBu)-Ser(Ψ$^{Me,Me}$pro)⁸-OH (0.8 eq) to CTC resin (0.25 g, 1.6 mmol/g) in presence of DIEA (3 eq) in DCM was carried out to give the loading 0.96 mmol/g. Then Fmoc-Phe-OH, Fmoc-Thr(tBu)-OH, Fmoc-Gly-OH, Fmoc-Glu(OtBu)-OH, Fmoc-Ala-OH, and Boc-His(Trt)-OH (three-fold excess with respect to the loading of the resin) were consecutively coupled to the resin in 60 min after pre-activation with DIC (3 eq) and OximaPure (3 eq). The first Fmoc deprotection was carried out using 20% solution of piperidine in DMF (3×2 ml, 3 min) with following washing of the resin with DMF (4×2 ml). For the Fmoc-deprotection of the other amino acids two treatments with 20% solution of piperidine in DMF (5 min and 15 min) were performed. The protected octapeptide was cleaved from the resin using the same procedure as described previously (see Step 2). Yield: 270 mg (80%), HPLC purity 87%

Step 5-a. Condensation of Fragments 3 and 4: Preparation of Liraglutide (1-31)

Fmoc-deprotected peptidyl resin-supported fragment 3 obtained in Step 3 (3-a or 3-b) was swelled in 2 ml of DMF. Protected fragment 4 (272 mg, 0.20 mmol, 1.5 eq) was dissolved in 7 ml of DMF, pre-activated with DIC (16 mg, 0.13 mmol), OxymaPure (40 mg, 0.27 mmol) and coupled to fragment 3. The reaction was stirred at 40° C. and monitored with HPLC. Another 1.5 eq of pre-activated fragment 3 (270 mg, 0.20 mmol) was added and stirred at 40° C. to complete the condensation. The resin was then washed with DMF (2×2 ml) and residual unreacted amino function was capped with 10% solution of Ac₂O in DMF (2 ml, 30 min). Then the resin was finally washed twice with DCM (2 ml) and dried.

Step 5-b. Condensation of Fragments 3 and 4 in the Presence of a Detergent: Preparation of Liraglutide (1-31)

Fmoc-deprotected resin-supported fragment 3 obtained in Step 3 (3-a or 3-b) was swelled in 2 ml of a mixture DMF:DCM 50:50 v/v+1% TX-100. Protected fragment 4 (270 mg, 0.195 mmol, 1.5 eq) was dissolved in 2.7 ml of DMF:DCM 50:50 v/v+1% TX-100, pre-activated with DIC (25 mg, 0.195 mmol), OxymaPure (28 mg, 0.195 mmol) and coupled to fragment 3. The reaction was stirred at 40° C. and monitored with HPLC. The resin was then washed with 2 ml of DMF:DCM 50:50 v/v+1% TX-100 and with DMF (2×2 ml). Residual unreacted amino function was capped with 10% solution of Ac₂O in DMF (2 ml, 30 min). Then the resin was finally washed twice with DCM (2 ml) and dried.

Step 6. Cleavage and Purification of Liraglutide

Dry peptidyl resin obtained in Step 5-a was suspended in 2 ml of the mixture TFA/water/phenol/TIS (v/v/v/v 88/5/5/2) and stirred for 4 h. Then the resin was filtered and washed with 1 ml of TFA. The solutions were collected and the crude peptide was precipitated in 5 ml of MTBE. The precipitate was washed several times with MTBE and dried to get crude liraglutide with overall yield 375 mg (75%) and HPLC purity 81%. The crude liraglutide was purified with mobile phase A 0.1% TFA/water and mobile phase B 0.1% TFA/acetonitrile. The fractions with purity greater than 99.0% were collected and lyophilized to afford purified liraglutide. HPLC purity: 99.4%, yield 112 mg (30%).

Example 2

Preparation of Semaglutide
Step 1. Preparation of Fragment 5, a Fragment D (17-31), 60 min. The introduction of the lipidated side chain into the peptide sequence was carried out using 1.5 eq of Fmoc-Lys[(tBuOOC—(CH$_2$)$_{16}$—CO-γGlu-OtBu)-AEEA-AEEA]-OH, which was pre-activated with 1.5 eq of DIC and 1.5 eq (SEQ ID No 13)

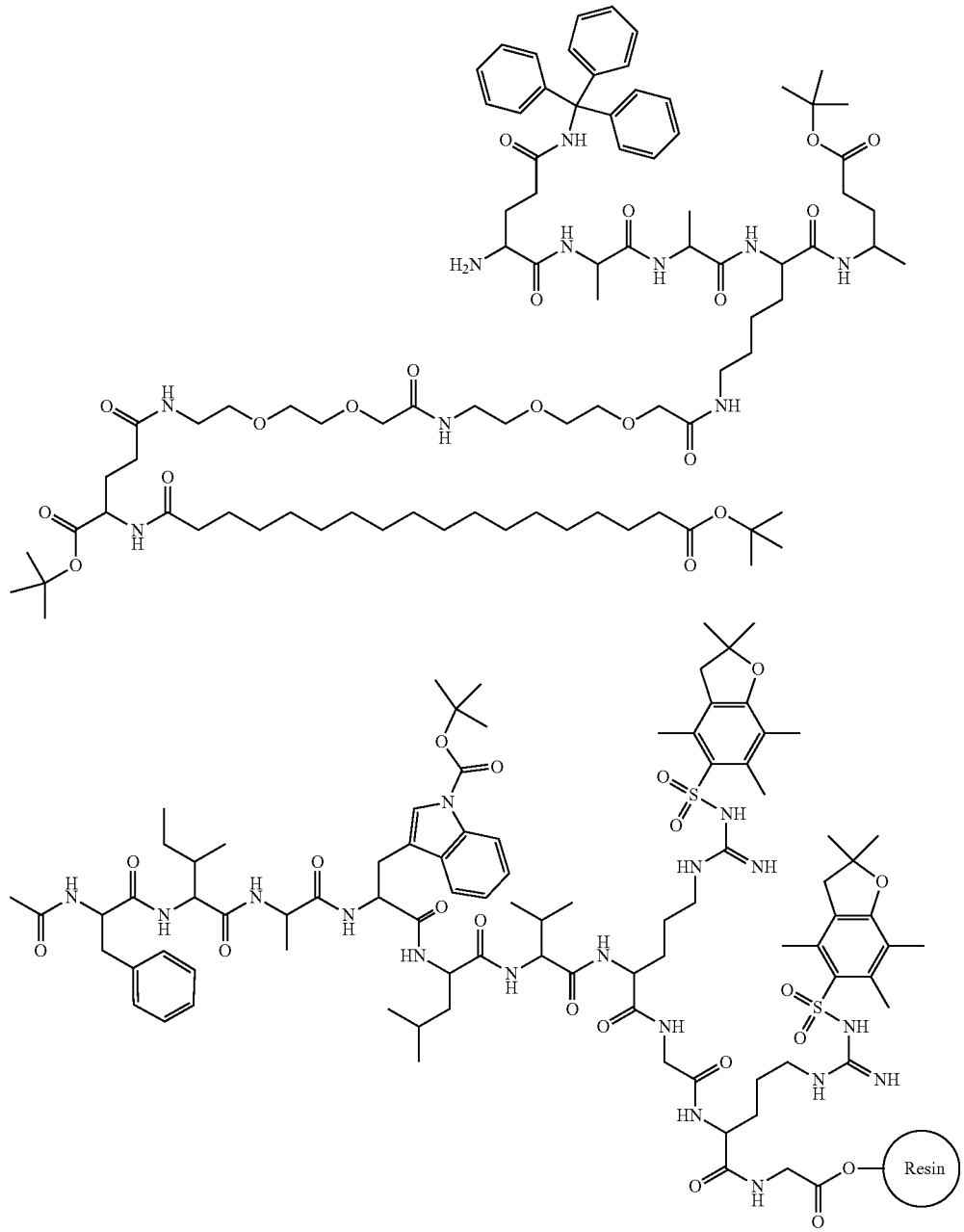

H-Gln(Trt)$^{17}$-Ala-Ala-Lys[(tBuOOC-(CH$_2$)$_{16}$-CO-γGlu-OtBu)-AEEA-AEEA]-Glu(OtBu)-Phe-Ile-Ala-Trp(N$^{in}$Boc)-Leu-Val-Arg(Pbf)-Gly-Arg(Pbf)-Gly$^{31}$-O-MBH Resin The synthesis of the peptide fragment 5 was carried out at room temperature using 0.5 g of H-Gly-O-MBH resin (loading 0.60 mmol/g). The resin was swelled in 3 ml of DMF and used for stepwise Fmoc SPPS. Fmoc-protected amino acids (two-fold excess respect to the loading of the resin) were pre-activated with the mixture of DIC (2 eq) and Oxyma-Pure (2 eq) during 3 min and consecutively coupled to the resin in 90 min. The couplings of Arg, Val, Trp, Ala$^{24}$, Phe and Gln were repeated with 1 eq of the coupling mixture for OxymaPure and coupled in 6 h at 40° C. The completion of the coupling was monitored by ninhydrine test. At the end of each coupling, the unreacted peptide chains were acetylated with acetic anhydride (3 eq) in DMF and washed with DMF (3×5 ml). The intermediate Fmoc deprotections were carried out using 20% solution of piperidine in DMF (2×5 ml, 10 min) with following washing of the resin with DMF (4×5 ml). After the completion of the synthesis the resin was washed with DCM and dried.

Step 2. Preparation of Fragment 2, a Fragment C (9-16), Fmoc-Asp(OtBu)⁹-Val-Ser(tBu)-Ser(tBu)-Tyr(tBu)-Leu-Glu(OtBu)-Gly¹⁶-OH (SEQ ID No 14) See Step 2. of Example 1.

Step 3. Condensation of Fragments 5 and 2 in the Presence of a Detergent: Preparation of Fragment 6, a Fragment B (9-31), DMF:DCM 50:50 v/v+1% TX-100 was pre-activated with DIC (16 mg, 0.56 mmol) and OxymaPure (88 mg, 0.56 mmol) at 40° C. during 15 min, then it was added to the resin and the reaction mixture was stirred for 3.5 h at 40° C. The completion of the coupling was monitored by ninhydrine test. The unreacted peptide chains were acetylated with 3 eq of acetic anhydride in DMF and then the peptide resin was (SEQ ID No 20)

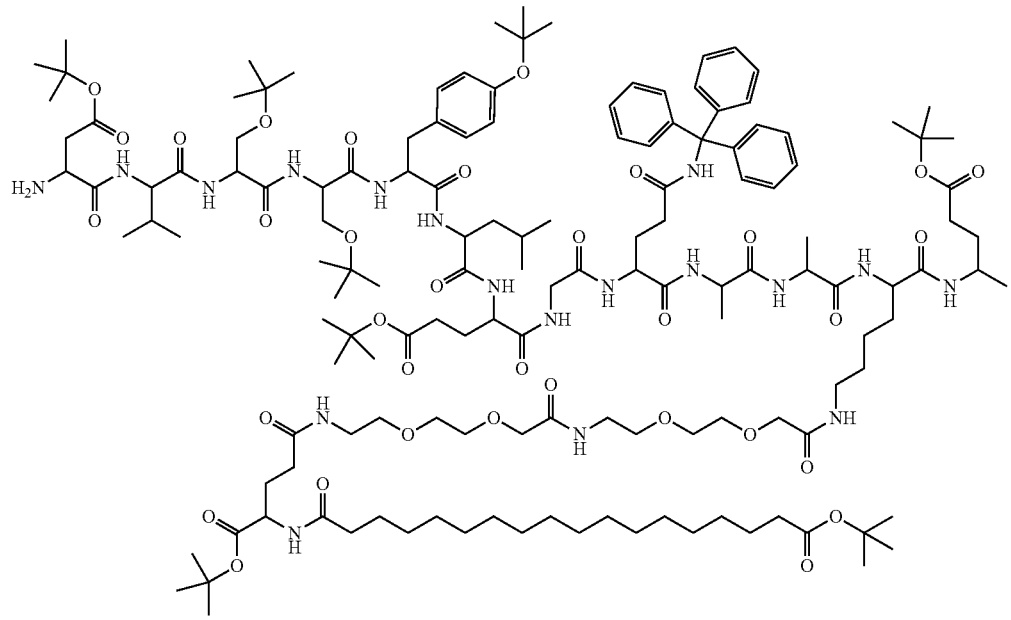

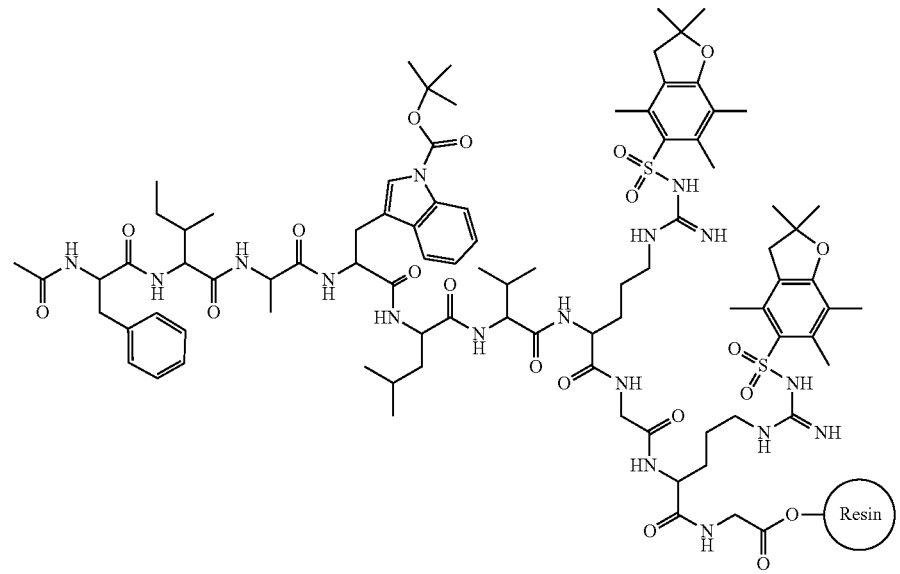

H-Asp(OtBu)⁹-Val-Ser(tBu)-Ser(tBu)-Tyr(tBu)-Leu-Glu(OtBu)-Gly-Gln(Trt)-Ala-Ala-Lys[(tBuOOC-(CH₂)₁₆-CO-γGlu-OtBu)-AEEA-AEEA]-Glu(OtBu)-Phe-Ile-Ala-Trp(Nⁱⁿالبoc)-Leu-Val-Arg(Pbf)-Gly-Arg(Pbf)-Gly³¹-MBH Resin Fmoc-deprotected resin with peptide fragment 5 obtained in Step 1 was swelled in 4 ml of a mixture DMF:DCM 50:50 v/v+1% TX-100 at 40° C. The solution of protected peptide fragment 2 (765 mg, 0.56 mmol, 2 eq) in 7 ml of mixture washed with DMF (3×5 ml). At the end, the Fmoc protective group was removed with 20% solution of piperidine in DMF (2×5 ml, 10 min) with following washing of the resin with DMF (4×5 ml).

Step 4. Preparation of Fragment 7, a Fragment A (1-8), (SEQ ID No 3)

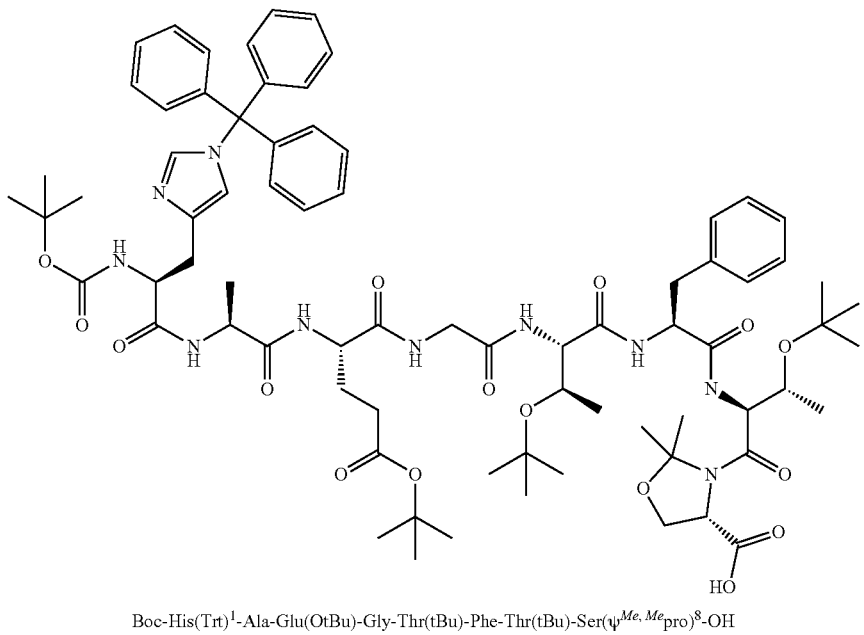

Boc-His(Trt)$^1$-Ala-Glu(OtBu)-Gly-Thr(tBu)-Phe-Thr(tBu)-Ser($\psi^{Me, Me}$pro)$^8$-OH The synthesis of peptide fragment 7 was carried out using 1 g of CTC resin (loading 1.6 mmol/g). After swelling of the resin in 10 ml of DCM, a solution of Fmoc-Thr(tBu)-Ser ($\psi^{Me,Me}$pro)$^8$-OH and DIEA (0.8 and 3 eq, respect to the loading of the resin) in 5 ml of DCM was added. The reaction mixture was stirred for 16 hours and the solvent was filtered off. The unreacted sites of the resin were capped using a solution of MeOH (3 eq) and DIEA (3 eq) in 5 ml of DCM for 15 minutes. After washing with DCM (2×10 ml) the resin was treated with a solution of acetic anhydride (3 eq) and DIEA (3 eq) in 10 ml of DCM for 15 minutes, washed with DMF (3×10 ml), DCM (3×10 ml) and dried. The loading of the resin was checked by UV adsorption measurement of the solution after Fmoc deprotection and was found to be 1.3 mmol/g. Then Fmoc-Phe-OH, Fmoc-Thr(tBu)-OH, Fmoc-Gly-OH, Fmoc-Glu(OtBu)-OH, Fmoc-Ala-OH, and Boc-His(Trt)-OH (2 eq) were pre-activated by 2 eq of DIC and 2 eq of OxymaPure during 3 min and coupled consecutively to the resin in 90 min. In the case of His, Oxyma-B replaced OxymaPure and pre-activation time was reduced to 1 min at 0° C. The intermediate Fmoc deprotections were carried out using 20% solution of piperidine in DMF (2×10 ml, 10 min) with following washing of the resin with DMF (4×10 ml). After the completion of the synthesis the resin was washed with DCM (2×10 ml) and dried. The protected peptide was cleaved from the resin by treatment with 3 ml of 1.5% TFA in DCM for 2 min and the solution was filtered into 3 ml of 10% solution of pyridine in methanol. The procedure was repeated 4 times and the combined solutions were concentrated to 30% of the volume. The protected peptide was precipitated by addition of water under ice-cold bath, filtered, washed several times by water and dried. Yield: 960 mg (77%).

Step 5. Condensation of Fragments 6 and 7: Preparation of Semaglutide (1-31)

Fmoc-deprotected peptidyl resin-supported fragment 6 obtained in the Step 3 was swelled in 2 ml of the mixture DMF:DCM 50:50 v/v+1% TX-100 at 40° C. The solution of protected peptide fragment 7 (780 mg, 0.56 mmol, 2 eq) in 7 ml of the mixture DMF:DCM 50:50 v/v+1% TX-100 was pre-activated with DIC (16 mg, 0.56 mmol) and OxymaPure (88 mg, 0.56 mmol) at 40° C. during 15 min. Then the coupling mixture was added to the resin and the reaction mixture was stirred for 3.5 h at 40° C. The completion of the coupling was monitored by ninhydrine test. The unreacted peptide chains were acetylated with 3 eq of acetic anhydride in DMF and peptide resin was washed with DMF (3×5 ml), DCM (2×5 ml) and dried.

Step 6. Cleavage and Purification of Semaglutide

Dry peptidyl resin obtained in Step 5 was suspended in 5 ml of the mixture TFA/water/phenol/TIS (v/v/v/v 88/5/5/2) and stirred for 1 h at 0° C. and 3 h at RT. Then the resin was filtered and washed with 1 ml of TFA. The solutions were collected and the crude peptide was precipitated in 25 ml of DIPE. The precipitate was washed several times with DIPE and dried to get crude semaglutide with overall yield 0.7 g (61%) and HPLC purity 74%. The crude semaglutide was purified with mobile phase A 0.1% TFA/water and mobile phase B 0.1% TFA/acetonitrile. The fractions with purity greater than 99.0% were collected and lyophilized to afford purified semaglutide. HPLC purity: 99.1%, yield 196 mg (28%).

The invention claimed is:

1. A fragment-based solid phase process for the preparation of a GLP-1 analogue of formula I $$HX_1EGTFTSDVSSYLEGQAAK(X_2)EFIAWLVR\text{-}GRG \quad (I)$$

wherein $X_1$ is Ala and $X_2$ is N-(1-oxohexadecyl)-L-γ-glutamyl, or $X_1$ is α-aminoisobutyric acid (Aib) and $X_2$ is N-(17-carboxy-1-oxoheptadecyl)-L-γ-glutamyl-2-[2-(2-aminoethoxy)ethoxy]acetyl-2-[2-(2-aminoethoxy)ethoxy]acetyl, wherein the process comprises a final coupling step between an N-terminal fragment A selected from the group consisting of:

His-$X_1$-Glu-Gly-Thr-Phe-Thr-Ser(ψ$^{z,z}$pro),
His-$X_1$-Glu-Gly-Thr-Phe-Thr-Ser-Asp-Val-Ser(ψ$^{z,z}$pro),
His-$X_1$-Glu-Gly-Thr-Phe-Thr-Ser-Asp-Val-Ser-Ser(ψ$^{z,z}$pro),
His-$X_1$-Glu-Gly-Thr-Phe-Thr(ψ$^{z,z}$pro),
and
His-$X_1$-Glu-Gly-Thr(ψ$^{z,z}$pro); wherein
$X_1$ is Ala or Aib, and
(ψ$^{z,z}$pro) comprises Ser or Thr which is pseudoproline protected according to the formula:

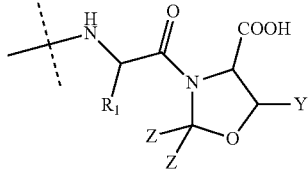

wherein
Y is hydrogen for Ser or is Me for Thr,
Z is hydrogen or Me, and
$R_1$ is the side-chain of the amino acid bonded to the pseudoproline protected amino acid;

and a C-terminal fragment B comprising the remaining amino acids of the GLP-1 analogue of formula I, wherein the side chain of one or more of the amino acids of fragment A and/or fragment B is optionally protected.

2. The process according to claim 1,
wherein fragment A is
Boc-His-$X_1$-Glu-Gly-Thr-Phe-Thr-Ser(ψ$^{Me,Me}$pro),
Boc-His-$X_1$-Glu-Gly-Thr-Phe-Thr-Ser-Asp-Val-Ser (ψ$^{Me,Me}$pro),
Boc-His-$X_1$-Glu-Gly-Thr-Phe-Thr-Ser-Asp-Val-Ser-Ser(ψ$^{Me,Me}$pro),
Boc-His-$X_1$-Glu-Gly-Thr-Phe-Thr(ψ$^{Me,Me}$pro)
or
Boc-His-$X_1$-Glu-Gly-Thr(ψ$^{Me,Me}$pro),
and fragment A is coupled to a protected peptide fragment B attached to a resin,
wherein fragment B is
Asp-Val-Ser-Ser-Tyr-Leu-Glu-Gly-Gln-Ala-Ala-Lys($X_2$)-Glu-Phe-Ile-Ala-
-Trp-Leu-Val-Arg-Gly-Arg-Gly-resin,
Ser-Tyr-Leu-Glu-Gly-Gln-Ala-Ala-Lys($X_2$)-Glu-Phe-Ile-Ala-
-Trp-Leu-Val-Arg-Gly-Arg-Gly-resin,
Tyr-Leu-Glu-Gly-Gln-Ala-Ala-Lys($X_2$)-Glu-Phe-Ile-Ala-
-Trp-Leu-Val-Arg-Gly-Arg-Gly-resin,
Ser-Asp-Val-Ser-Ser-Tyr-Leu-Glu-Gly-Gln-Ala-Ala-Lys($X_2$)-Glu-Phe-Ile-Ala-
-Trp-Leu-Val-Arg-Gly-Arg-Gly-resin
or
Phe-Thr-Ser-Asp-Val-Ser-Ser-Tyr-Leu-Glu-Gly-Gln-Ala-Ala-Lys($X_2$)-Glu-Phe-Ile-Ala-
-Trp-Leu-Val-Arg-Gly-Arg-Gly-resin.

3. The process according to claim 2, wherein the preparation of fragment B comprises coupling a fragment C with a fragment D, wherein
fragment C is
Asp-Val-Ser-Ser-Tyr-Leu-Glu-Gly,
Ser-Tyr-Leu-Glu-Gly,
Tyr-Leu-Glu-Gly, Ser-Asp-Val-Ser-Ser-Tyr-Leu-Glu-Gly
or
Phe-Thr-Ser-Asp-Val-Ser-Ser-Tyr-Leu-Glu-Gly,
and fragment D is
Gln$^{17}$-Ala-Ala-Lys(X$_2$)-Glu-Phe-Ile-Ala-Trp-Leu-Val-Arg-Gly-Arg-Gly$^{31}$-resin.

4. The process according to claim 1, wherein X$_1$ is Ala and X$_2$ is N-(1-oxohexadecyl)-L-γ-glutamyl.

5. The process according to claim 1, wherein X$_1$ is Aib and X$_2$ is N-(17-carboxy-1-oxoheptadecyl)-L-γ-glutamyl-2-[2-(2-aminoethoxy)ethoxy]acetyl-2-[2-(2-aminoethoxy)ethoxy]acetyl.

6. The process according to claim 3, wherein fragment C is
Fmoc-Asp(OtBu)$^9$-Val-Ser(tBu)-Ser(tBu)-Tyr(tBu)-Leu-Glu(OtBu)-Gly$^{16}$-OH,
Fmoc-Ser(tBu)-Tyr(tBu)-Leu-Glu(OtBu)-Gly$^{16}$-OH,
Fmoc-Tyr(tBu)-Leu-Glu(OtBu)-Gly$^{16}$-OH,
Fmoc-Ser(tBu)-Asp(OtBu)$^9$-Val-Ser(tBu)-Ser(tBu)-Tyr(tBu)-Leu-Glu(OtBu)-Gly$^{16}$-OH
or
Fmoc-Phe-Thr(tBu)-Ser(tBu)-Asp(OtBu)$^9$-Val-Ser(tBu)-Ser(tBu)-Tyr(tBu)-Leu-Glu(OtBu)-Gly$^{16}$-OH,
and fragment D is
H-Gln(Trt)$^{17}$-Ala-Ala-Lys(Pal-Glu-OtBu)-Glu(OtBu)-Phe-Ile-Ala-Trp(N$^{in}$Boc)-Leu-Val-Arg(Pbf)-Gly-Arg(Pbf)-Gly$^{31}$-Wang resin, or
H-Gln(Trt)$^{17}$-Ala-Ala-Lys[(tBuOOC—(CH$_2$)$_{16}$—CO-γGlu-OtBu)-AEEA-AEEA]-Glu(OtBu)-Phe-Ile-Ala-Trp(N$^{in}$Boc)-Leu-Val-Arg(Pbf)-Gly-Arg(Pbf)-Gly$^{31}$-O-MBH resin.

7. The process according to claim 6, wherein fragment C is
Fmoc-Asp(OtBu)$^9$-Val-Ser(tBu)-Ser(tBu)-Tyr(tBu)-Leu-Glu(OtBu)-Gly$^{16}$-OH
and fragment D is
H-Gln(Trt)$^{17}$-Ala-Ala-Lys(Pal-Glu-OtBu)-Glu(OtBu)-Phe-Ile-Ala-Trp(NnBoc)-Leu-Val-Arg(Pbf)-Gly-Arg(Pbf)-Gly$^{31}$-Wang resin, or
H-Gln(Trt)$^{17}$-Ala-Ala-Lys[(tBuOOC—(CH$_2$)$_{16}$—CO-γGlu-OtBu)-AEEA-AEEA]-Glu(OtBu)-Phe-Ile-Ala-Trp(N$^{in}$Boc)-Leu-Val-Arg(Pbf)-Gly-Arg(Pbf)-Gly$^{31}$-O-MBH resin.

8. The process according to claim 2, wherein fragment A is
Boc-His-Ala-Glu-Gly-Thr-Phe-Thr-Ser(ψ$^{Me,Me}$pro) or
Boc-His-Aib-Glu-Gly-Thr-Phe-Thr-Ser(ψ$^{Me,Me}$pro)
and fragment B is
Asp-Val-Ser-Ser-Tyr-Leu-Glu-Gly-Gln-Ala-Ala-Lys(Pal-Glu)-Glu-Phe-Ile-Ala-
-Trp-Leu-Val-Arg-Gly-Arg-Gly-resin, or
Asp-Val-Ser-Ser-Tyr-Leu-Glu-Gly-Gln-Ala-Ala-Lys[(ROOC—(CH$_2$)$_{16}$—CO-γGlu-OR')-AEEA-AEEA]-Glu-Phe-Ile-Ala-Trp-Leu-Val-Arg-Gly-Arg-Gly-resin,
wherein R and R' are the same or different, and each is a carboxylic acid protective group.

9. The process according to claim 8, wherein fragment A is
Boc-His(Tr)$^1$-Ala-Glu(OtBu)-Gly-Thr(tBu)-Phe-Thr(tBu)-Ser(ψ$^{Me,Me}$pro)$^8$-OH or
Boc-His(Tr)$^1$-Aib-Glu(OtBu)-Gly-Thr(tBu)-Phe-Thr(tBu)-Ser(ψ$^{Me,Me}$pro)$^8$-OH,
and fragment B is
H-Asp(OtBu)$^9$-Val-Ser(tBu)-Ser(tBu)-Tyr(tBu)-Leu-Glu(OtBu)-Gly-Gln(Trt)-Ala-Ala-Lys(Pal-Glu-OtBu)-Glu(OtBu)-Phe-Ile-Ala-Trp(N$^{in}$Boc)-Leu-Val-Arg(Pbf)-Gly-Arg(Pbf)-Gly$^{31}$-Wang resin, or
H-Asp(OtBu)$^9$-Val-Ser(tBu)-Ser(tBu)-Tyr(tBu)-Leu-Glu(OtBu)-Gly-Gln(Trt)-Ala-Ala-Lys[(tBuOOC—(CH$_2$)$_{16}$—CO-γGlu-OtBu)-AEEA-AEEA]-Glu-(OtBu)-Phe-Ile-Ala-Trp(N$^{in}$Boc)-Leu-Val-Arg(Pbf)-Gly-Arg(Pbf)-Gly$^{31}$-MBH resin.

10. The process according to claim 9, wherein preparation of fragment B comprises coupling
Fmoc-Asp(OtBu)$^9$-Val-Ser(tBu)-Ser(tBu)-Tyr(tBu)-Leu-Glu(OtBu)-Gly$^{16}$-OH with
H-Gln(Trt)$^{17}$-Ala-Ala-Lys(Pal-Glu-OtBu)-Glu(OtBu)-Phe-Ile-Ala-Trp(N$^{in}$Boc)-Leu-Val-Arg(Pbf)-Gly-Arg(Pbf)-Gly$^{31}$-Wang resin, or
H-Gln(Trt)$^{17}$-Ala-Ala-Lys[(tBuOOC—(CH$_2$)$_{16}$—CO-γGlu-OtBu)-AEEA-AEEA]-Glu-(OtBu)-Phe-Ile-Ala-Trp(N$^{in}$Boc)-Leu-Val-Arg(Pbf)-Gly-Arg(Pbf)-Gly$^{31}$-MBH resin.

11. The process according to claim 1, wherein the coupling of fragments is carried out in the presence of N,N'-diisopropylcarbodiimide and ethyl 2-cyano-2-hydroxyimino-acetate.

12. The process according to claim 1, wherein the coupling of fragments is carried out at a temperature in the range of 10-70° C.

13. The process according to claim 1, wherein the coupling of fragments is carried out in the presence of a detergent.

14. The process according to claim 1, wherein the GLP-1 analogue of formula I is attached to a resin, and the process further comprises deprotection and cleavage of the GLP-1 analogue of formula I from the resin.

15. The process according to claim 1, wherein the process further comprises purification of the GLP-1 analogue of formula I by chromatography.

* * * * *